US012478508B2

(12) United States Patent
Deibel et al.

(10) Patent No.: US 12,478,508 B2
(45) Date of Patent: Nov. 25, 2025

(54) TUBE DEPLOYING SYSTEM

(71) Applicant: Preceptis Medical, Inc., Maple Grove, MN (US)

(72) Inventors: Rudolf Andreas Deibel, Eden Prairie, MN (US); Andrew N. Smith, Maple Grove, MN (US); Paul M. Goudreau, Edina, MN (US)

(73) Assignee: Preceptis Medical, Inc., Golden Valley, MN (US)

( * ) Notice: Subject to any disclaimer, the term of this patent is extended or adjusted under 35 U.S.C. 154(b) by 690 days.

(21) Appl. No.: 17/563,537

(22) Filed: Dec. 28, 2021

(65) Prior Publication Data

US 2022/0202618 A1 Jun. 30, 2022

Related U.S. Application Data

(60) Provisional application No. 63/132,562, filed on Dec. 31, 2020.

(51) Int. Cl.
*A61F 11/20* (2022.01)

(52) U.S. Cl.
CPC .................................. *A61F 11/202* (2022.01)

(58) Field of Classification Search
CPC ...... A61F 11/20; A61F 11/202; A61F 11/006; A61F 11/00; A61F 2/95; A61F 2/9517; A61B 17/32056; A61B 2017/2212; A61B 2017/2215; A61B 17/22; B26B 5/001
See application file for complete search history.

(56) References Cited

U.S. PATENT DOCUMENTS

| | | | |
|---|---|---|---|
| 3,020,912 | A | 2/1962 | Chester |
| 3,530,860 | A | 9/1970 | Majoros |
| 3,662,754 | A | 5/1972 | Halloran |
| 3,807,409 | A | 4/1974 | Paparella et al. |
| 3,871,380 | A | 3/1975 | Heros |

(Continued)

FOREIGN PATENT DOCUMENTS

| | | | |
|---|---|---|---|
| CN | 102014795 | A | 4/2011 |
| GB | 2437708 | A | 11/2007 |

(Continued)

OTHER PUBLICATIONS

Australian Examination Report dated Jul. 18, 2013 for Australian application No. 2009215468, 4 pages.

(Continued)

*Primary Examiner* — Sarah A Long
*Assistant Examiner* — James R McGinnity
(74) *Attorney, Agent, or Firm* — Leanne Taveggia Farrell; Westman, Champlin & Koehler, P.A.

(57) ABSTRACT

A tube deploying system includes a nose assembly having a distal cutting edge and a tube. The distal cutting edge is configured to be manually advanced to pierce a membrane of a patient. A handle of the system includes a pull mechanism having a slider and a pull block and an actuation member having a distal end that couples to the distal cutting edge and a proximal end that couples to the pull block. The slider is manually operated to move the pull mechanism from a non-pulled configuration to a pulled configuration. In the pulled configuration, the pull block pulls the actuation member such that the distal cutting edge is retracted to deploy the tube.

18 Claims, 36 Drawing Sheets

(56) References Cited

U.S. PATENT DOCUMENTS 3,888,258 A 6/1975 Akiyama
3,897,786 A 8/1975 Garnett et al.
3,913,584 A 10/1975 Walchle et al.
3,948,271 A 4/1976 Akiyama
4,174,716 A 11/1979 Treace
4,334,538 A 6/1982 Juhn
4,445,517 A 5/1984 Feild
4,468,218 A 8/1984 Armstrong
4,473,073 A 9/1984 Darnell
4,580,568 A 4/1986 Gianturco
4,695,275 A 9/1987 Bruce et al.
4,744,792 A 5/1988 Sander et al.
4,964,850 A 10/1990 Bouton et al.
5,026,378 A 6/1991 Goldsmith, III
5,053,040 A 10/1991 Goldsmith, III
5,073,166 A 12/1991 Parks et al.
5,139,502 A 8/1992 Berg et al.
5,178,623 A 1/1993 Cinberg et al.
5,207,685 A 5/1993 Cinberg et al.
5,254,120 A 10/1993 Cinberg et al.
5,466,239 A 11/1995 Cinberg et al.
5,484,434 A 1/1996 Cartmell et al.
5,496,329 A 3/1996 Reisinger
5,566,094 A 10/1996 Kojima et al.
5,578,053 A 11/1996 Yoon
5,601,568 A 2/1997 Chevillon et al.
5,643,280 A 7/1997 Del Rio et al.
5,645,584 A 7/1997 Suyama
5,665,094 A 9/1997 Goldenberg
5,693,065 A 12/1997 Rains, III
D389,915 S 1/1998 Emerson et al.
5,709,677 A 1/1998 Slatkine
5,711,309 A 1/1998 Goldenberg
5,916,150 A 6/1999 Sillman
5,976,151 A 11/1999 Siegbahn
6,027,532 A 2/2000 Hobeika
D439,337 S 3/2001 Jones
6,238,402 B1 5/2001 Sullivan, III et al.
6,245,077 B1 6/2001 East et al.
6,258,067 B1 7/2001 Hill
6,292,702 B1 9/2001 King et al.
D453,833 S 2/2002 Hess
6,361,526 B1 3/2002 Reisdorf et al.
6,390,975 B1 5/2002 Walls et al.
6,406,453 B1 6/2002 Goode et al.
6,443,970 B1 9/2002 Schulze et al.
6,450,937 B1 9/2002 Mercereau et al.
6,527,780 B1 3/2003 Wallace et al.
6,692,455 B2 2/2004 Goode et al.
6,695,861 B1 2/2004 Rosenberg et al.
D490,152 S 5/2004 Myall et al.
6,730,056 B1 5/2004 Ghaem et al.
6,770,080 B2 8/2004 Kaplan et al.
6,776,797 B1 8/2004 Blom et al.
6,936,023 B2 8/2005 Goode et al.
6,939,494 B2 9/2005 Goode et al.
D521,641 S 5/2006 Reschke et al.
D538,936 S 3/2007 Böhmel et al.
7,235,099 B1 6/2007 Duncavage et al.
7,410,480 B2 8/2008 Muni et al.
7,419,497 B2 9/2008 Muni et al.
7,704,259 B2 4/2010 Kaplan et al.
D619,579 S 7/2010 Vieira
7,854,743 B2 12/2010 Palasis et al.
7,879,033 B2 2/2011 Sartor et al.
8,052,693 B2 11/2011 Shahoian
D664,657 S 7/2012 Vieira et al.
D673,676 S 1/2013 Goudreau et al.
8,574,240 B2 11/2013 Loushin et al.
8,864,774 B2 10/2014 Liu et al.
8,979,868 B2 3/2015 Loushin et al.
9,011,363 B2 4/2015 Clopp et al.
9,023,059 B2 5/2015 Loushin et al.
9,370,448 B2 6/2016 Loushin et al.
9,532,802 B2 1/2017 Konstorum et al.
9,782,298 B2 10/2017 Loushin et al.
9,907,700 B2 3/2018 Clopp et al.
10,624,792 B2 4/2020 Loushin et al.
10,695,224 B2 6/2020 Loushin et al.
10,792,189 B2 10/2020 Leland et al.
2002/0058899 A1 5/2002 Goode et al.
2002/0099375 A1* 7/2002 Hess .................. A61B 18/1445 606/51
2003/0018291 A1 1/2003 Hill et al.
2005/0004520 A1 1/2005 Lemoine et al.
2005/0049675 A1 3/2005 Wallace
2005/0256450 A1 11/2005 Palasis et al.
2006/0025793 A1 2/2006 Gibson et al.
2006/0116607 A1 6/2006 Nakamura et al.
2006/0116692 A1* 6/2006 Ward ................. A61B 17/2909 606/113
2008/0051804 A1 2/2008 Cottler et al.
2008/0097295 A1 4/2008 Makower et al.
2008/0234708 A1 9/2008 Houser et al.
2008/0262468 A1 10/2008 Clifford et al.
2008/0262505 A1 10/2008 Shahoian
2008/0262508 A1 10/2008 Clifford et al.
2008/0262509 A1 10/2008 Clifford et al.
2008/0262510 A1 10/2008 Clifford
2009/0275955 A1 11/2009 Kutluhan
2009/0299141 A1 12/2009 Downey et al.
2009/0299379 A1 12/2009 Katz et al.
2010/0174290 A1 7/2010 Wuebbeling et al.
2010/0256653 A1 10/2010 Kaplan et al.
2011/0015645 A1 1/2011 Liu et al.
2011/0282190 A1 11/2011 Caffey et al.
2011/0288559 A1 11/2011 Shahoian
2013/0338678 A1* 12/2013 Loushin ................ A61F 11/202 606/109
2015/0290040 A1* 10/2015 Vaughan ............... A61F 11/202 606/109
2018/0000326 A1* 1/2018 Grant ................... A61B 1/3132
2019/0374751 A1* 12/2019 Finson ............ A61M 25/10182
2020/0237559 A1 7/2020 Loushin
2020/0281772 A1 9/2020 Loushin

FOREIGN PATENT DOCUMENTS

WO 3057082 A1 7/2003
WO 2008131195 A2 10/2008
WO 2009105619 A1 8/2009
WO 2012094666 A1 7/2012
WO 2014075949 A1 5/2014
WO 2016025310 A1 2/2016

OTHER PUBLICATIONS

Canadian Office Action dated Nov. 12, 2019 for Canadian application No. 2,876,865, 5 pages.
Canadian Office Action dated Apr. 16, 2020 for Canadian application No. 2,876,865.
Canadian Office Action dated Apr. 5, 2019 for Canadian application No. 2,876,865, 4 pages.
Canadian Office Action dated Feb. 3, 2015 for Canadian application No. 2,716,040, 5 pages.
Chinese Office Action dated Jan. 28, 2014 for Chinese application No. 200980113954.0, with English translation, 16 pages.
Chinese Office Action dated Nov. 18, 2015 for Chinese application No. 201380031471.2, including English translation, 14 pages.
Chinese Office Action dated Dec. 4, 2012 for Chinese application No. 200980113954.0, with English translation, 7 pages.
Chinese Office Action dated Jul. 11, 2014 for Chinese application No. 200980113954.0, with English translation, 9 pages.
Chinese Office Action dated Jul. 22, 2013 for Chinese application No. 200980113954.0, with English translation, 9 pages.
Chinese Office Action dated Jul. 7, 2016 for Chinese application No. 201380031471.2, with English translation, 13 pages.
European Commuication dated Sep. 13, 2011 for European application No. 09713274.0, 1 page.
European Communcation dated Apr. 29, 2015 for European application No. 13733138.5, 2 pages.

(56) References Cited

OTHER PUBLICATIONS

European Communication dated Apr. 18, 2017 for European application No. 09713274.0, 5 pages.
European Extended Search Report dated Aug. 25, 2011 for European application No. 09713274.0, 7 pages.
European Office Action dated Feb. 24, 2016 for European application No. 09713274.0, 4 pages.
European Office Action dated May 25, 2018 for European application No. 13733138.5, 4 pages.
European Summons to attend oral proceedings pursuant to Rule 115(1) EPC dated Jul. 1, 2021 for European application No. 13733138.5, 6 pages.
Indian First Examination Report dated Jun. 26, 2020 for Indian application No. 67/MUMNP/2015, 8 pages.
Indian Office Action dated Feb. 22, 2018 for Indian application No. 5199/CHENP/2010, with English translation, 6 pages.
Korean Office Action dated Jun. 20, 2019 for Korean application No. 10-2015-7000954, with English translation, 5 pages.
Search Report and Written Opinion dated Oct. 1, 2009 for International application No. PCT/US2009/034648, 13 pages.
Search Report and Written Opinion dated Apr. 25, 2012 for International application No. PCT/US2012/020629, 13 pages.
Search Report and Written Opinion dated Sep. 18, 2013 from International application No. PCT/US2013/045082, 13 pages.
Prosecution history of corresponding U.S. Appl. No. 13/346,245 including: Non-Final Office Action dated Mar. 25, 2013 and Notice of Allowance and Examiner-Initiated Interview Summary dated Jul. 2, 2013.
PCT Notification of Transmittal of the International Search Report and the Written Opinion of the International Searching Authority, or the Declaration, International Search Report and Written Opinion dated Apr. 29, 2022.

* cited by examiner

TUBE DEPLOYING SYSTEM

CROSS-REFERENCE TO RELATED APPLICATION

The present application is based on and claims the benefit of U.S. provisional patent application Ser. No. 63/132,562, filed Dec. 31, 2020, the content of which is hereby incorporated by reference in its entirety.

SUMMARY

A tube deploying system includes a nose assembly having a distal cutting edge and a tube. The distal cutting edge is configured to be manually advanced to pierce a membrane of a patient. A handle of the system includes a pull mechanism having a slider and a pull block and an actuation member. The actuation member has a distal end that couples to the distal cutting edge and a proximal end that couples to the pull block. The slider is manually operated to move the pull mechanism from a non-pulled configuration to a pulled configuration. In the pulled configuration, the pull block pulls the actuation member such that the distal cutting edge is retracted to deploy the tube.

A pull mechanism on a tube deploying system includes a slider having a trigger portion that is manually operated to move the pull mechanism from a non-pulled configuration to a pulled configuration. The trigger portion of the slider includes a first peaked zone, a second peaked zone that has a height that is greater than a height of the first peaked zone and a valleyed zone located between the first peaked zone and the second peaked zone. The valleyed zone has a height that is less than the height of the first peaked zone and the height of the second peaked zone. The trigger portion further includes a rear guide zone located behind the second peaked zone. The first peaked zone, the second peaked zone and the valleyed zone include a plurality of raised features and the rear guide zone is free of the plurality of raised features.

A method of deploying a tube in a membrane includes providing a nose assembly that includes a nose portion, an elongated portion, a distal cutting edge and a tube. At least some of the elongated portion, the distal cutting edge and the tube are manually advanced in an orifice of a patient, a membrane of the patient is pierced with the distal cutting edge and a trigger portion on a slider of a pull mechanism is manually moved to pull an actuation member having a distal end coupled to the distal cutting edge to retract the distal cutting edge and to deploy the tube. The slider is configured to rotate a pivot arm about a fixed pivot point. The pivot arm is coupled to a pull block that is connected to a proximal end of the actuation member.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION

The tube deploying systems described herein combine the steps of making an incision in a membrane, such as a myringotomy in a tympanic membrane or eardrum, positioning a tube (e.g., ventilation tube such as a pressure equalization (PE) tube or tympanostomy tube that may have a variety of different geometries including cylindrical, rectangular or other types of cross sections) and placing or inserting the tube in a patient's membrane in a single system. In the embodiments described, each tube deploying system includes a nose assembly connected to a handle and a pull mechanism that both protrudes from the handle and is housed in the handle. Backlash is clearance or lost motion in a mechanical system caused by gaps between the parts. In other words, backlash is the maximum distance or angle that any part in the mechanical system may move in one direction without applying any sort of appreciable force onto the next or sequential part in the mechanical system. The tube deploying system described below includes an overall mechanical design that minimizes backlash. Because a clinician often blindly grasps the described tube deploying systems to use, the haptics of the described tube deploying systems, both in the mechanisms and on their surfaces, are important for user functionality.

Figure 1:
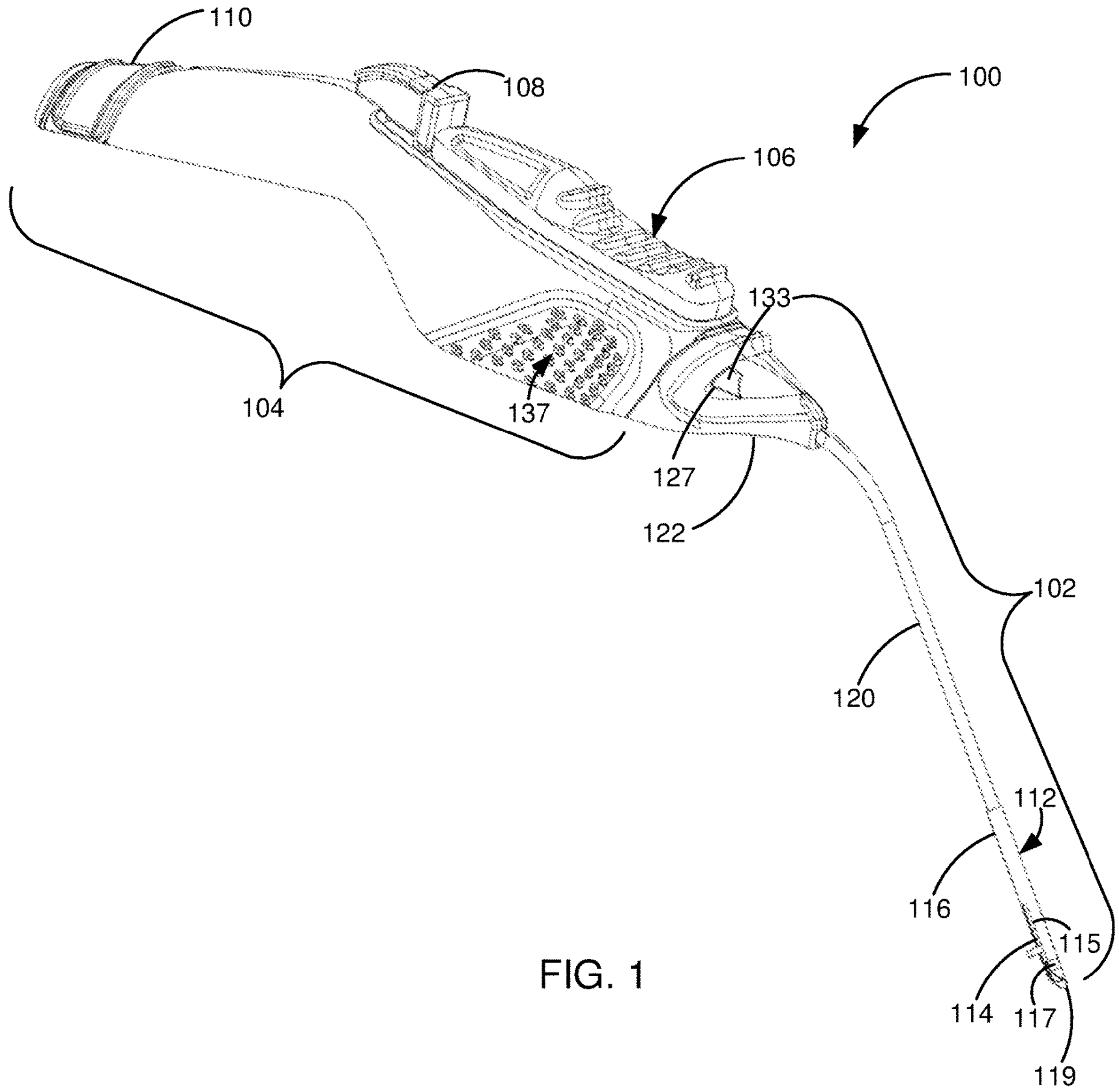
FIG. 1 is a front perspective view of a tube deploying system having a cutting sheath slot facing in a first direction according to an embodiment.
Figure 2:
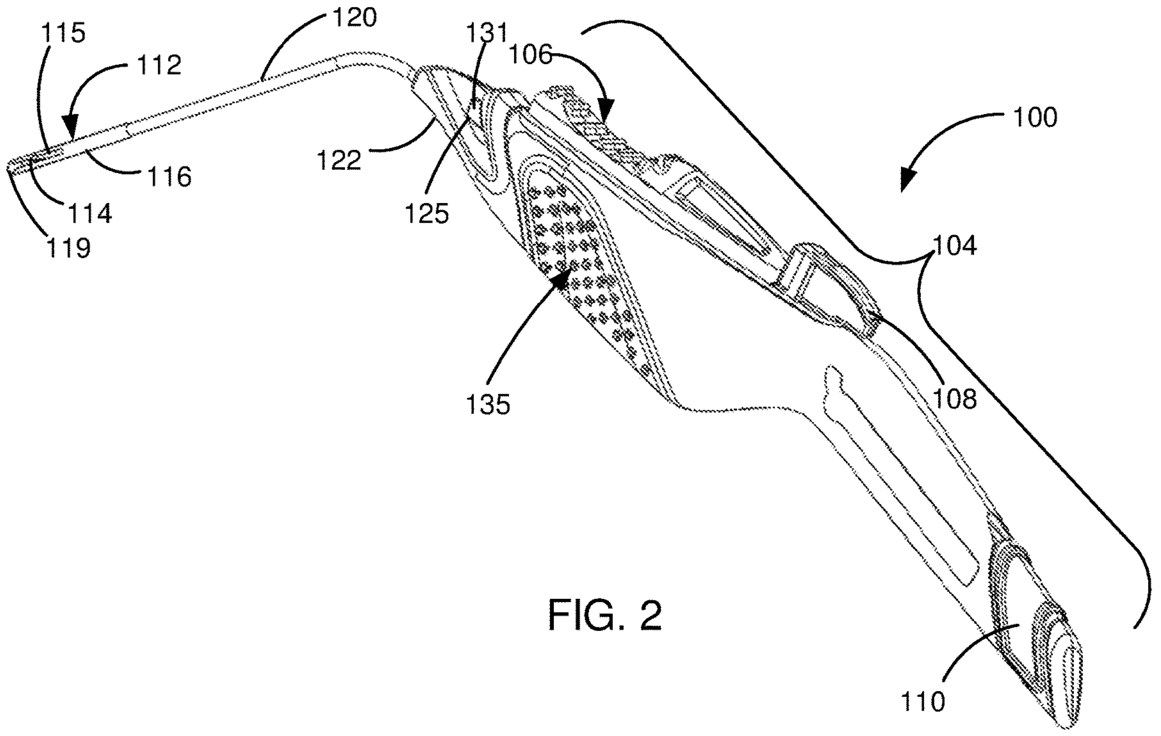
FIG. 2 is back perspective view of the tube deploying system illustrated in FIG. 1 but with the cutting sheath slot facing in a second direction according to an embodiment.
Figure 3:
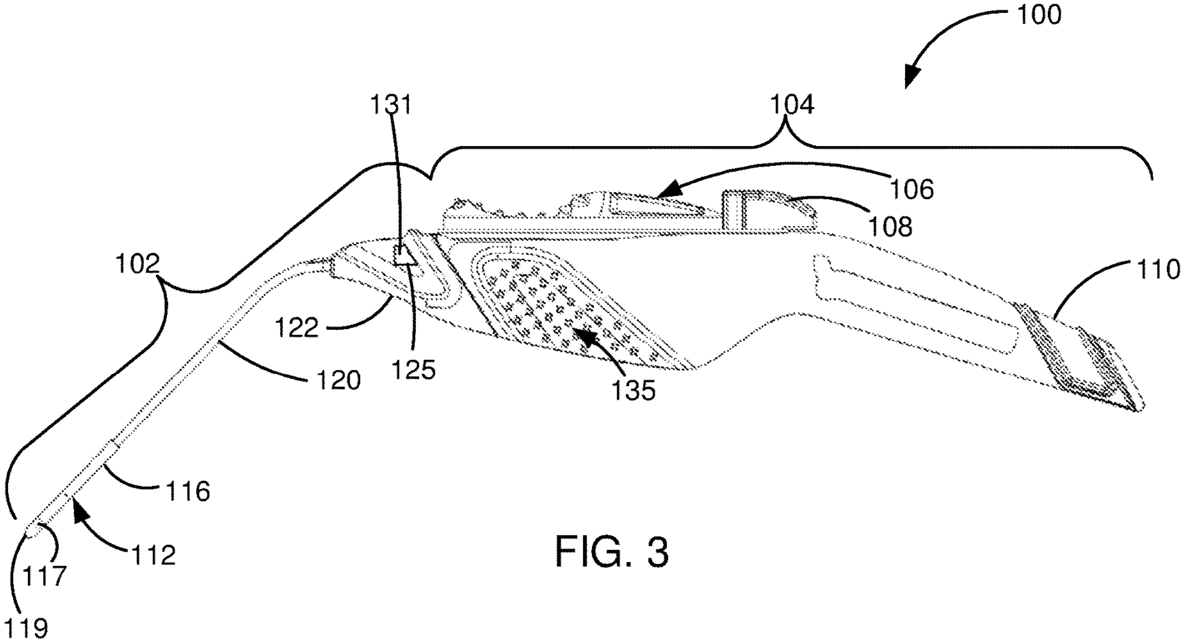
FIG. 3 is a right side view of FIG. 1.
Figure 4:
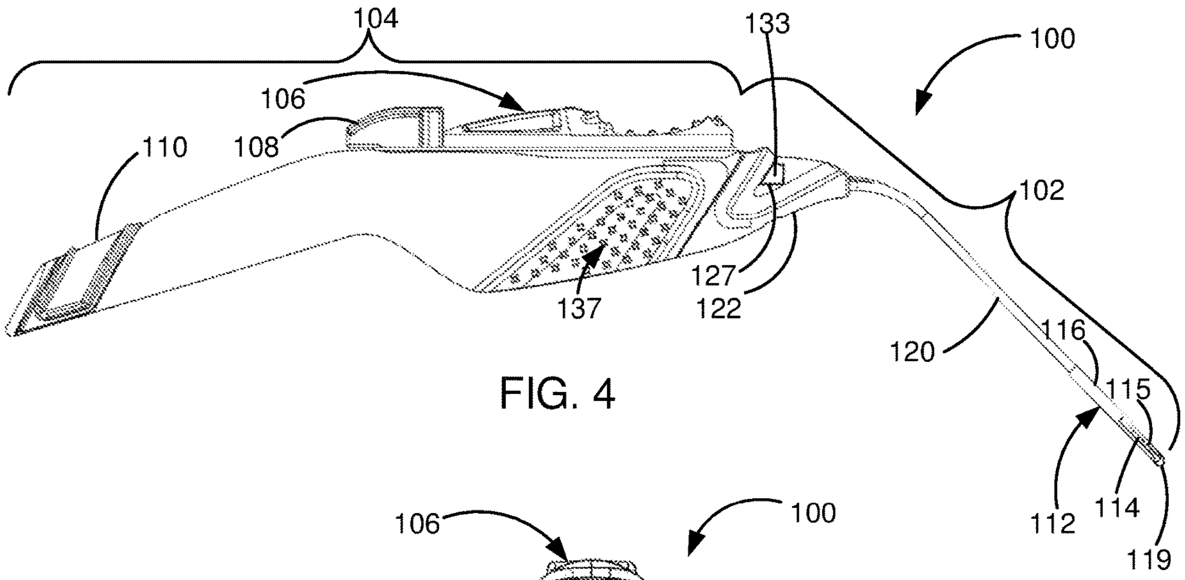
FIG. 4 is a left side view of FIG. 1.
Figure 5:
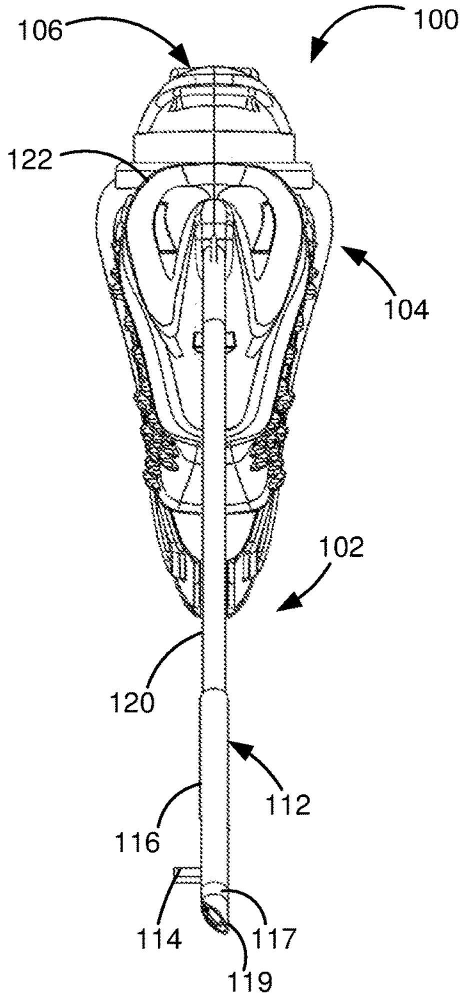
FIG. 5 is a front view of FIG. 1.
Figure 6:
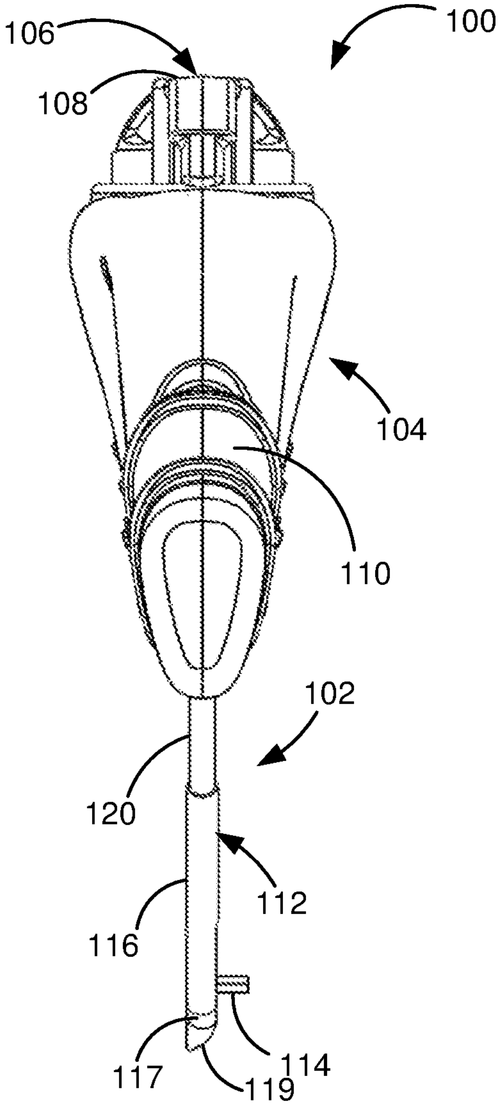
FIG. 6 is a back view of FIG. 1.
Figure 7:
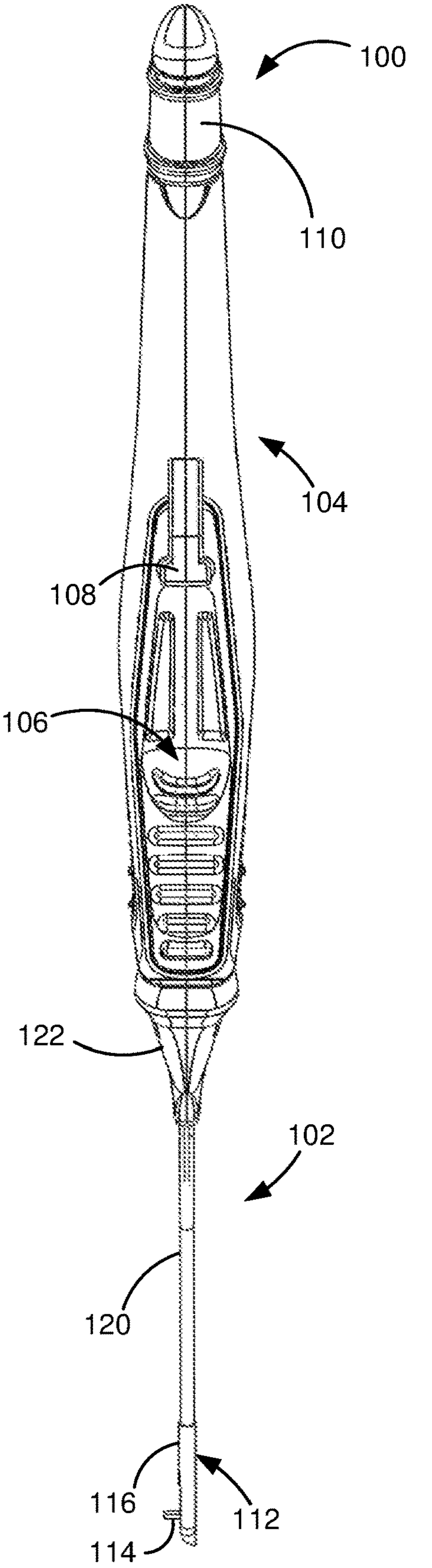
FIG. 7 is a top view of FIG. 1.
Figure 8:
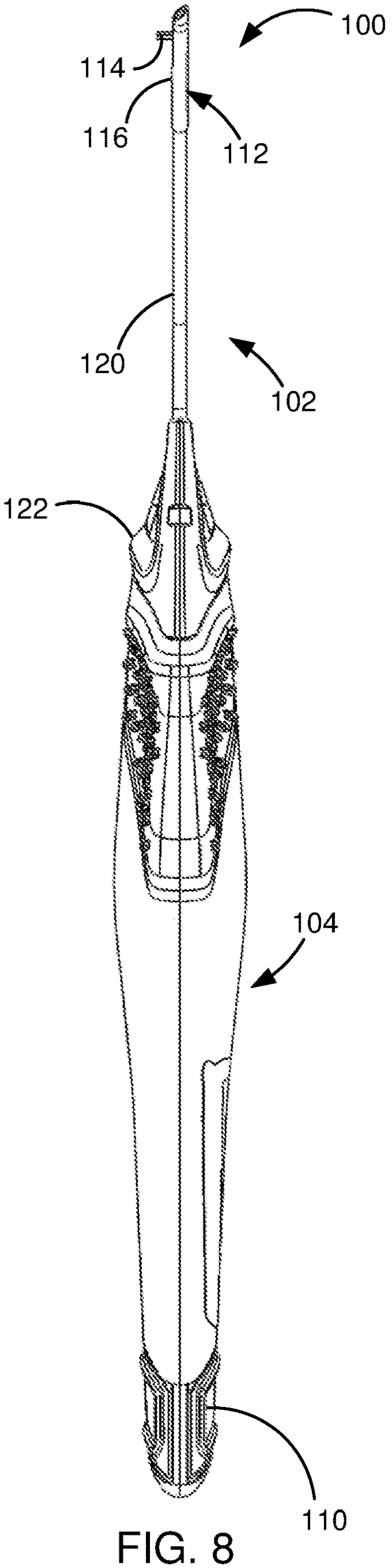
FIG. 8 is a bottom view of FIG. 1.
Figure 9:
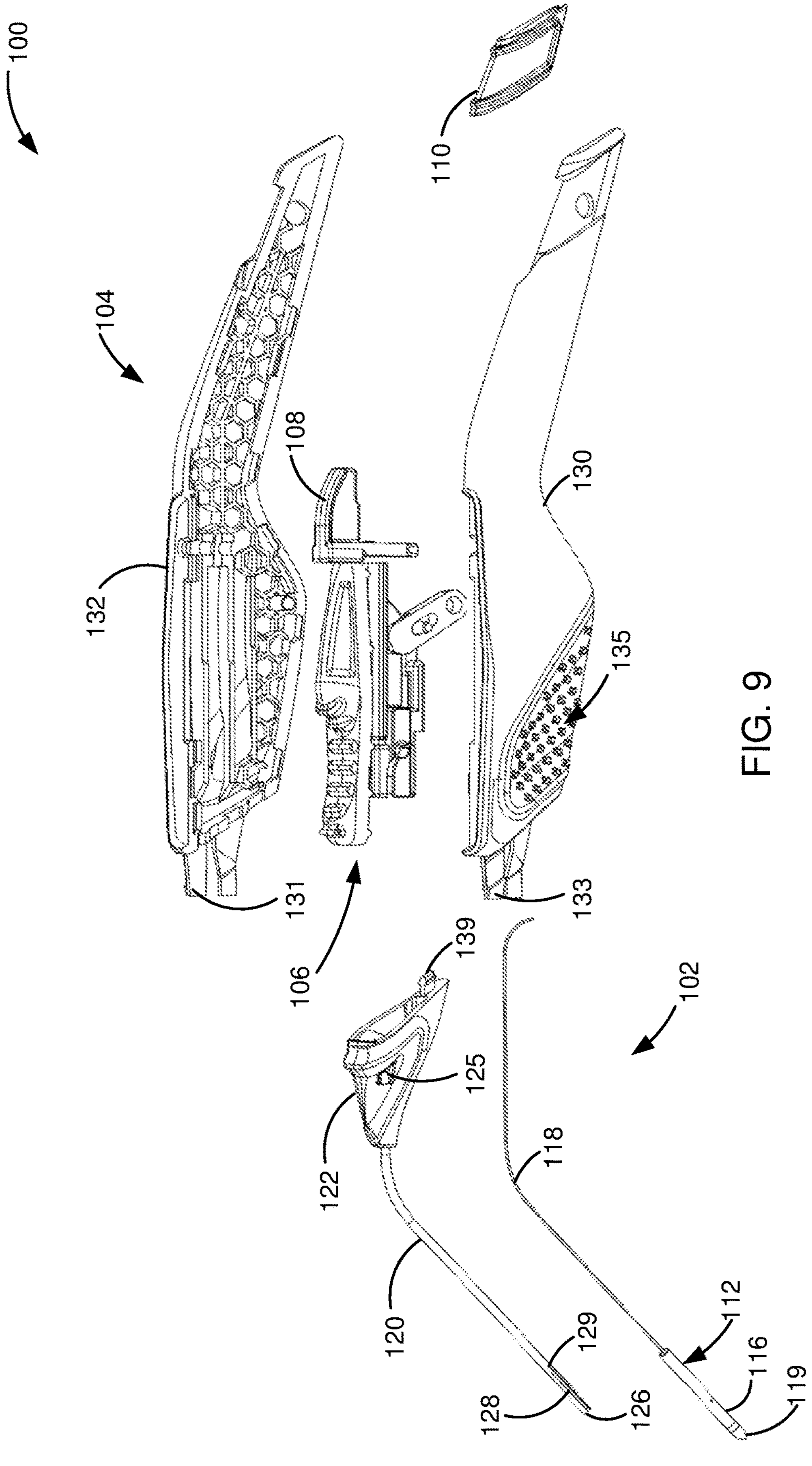
FIG. 9 is an exploded view of FIG. 1.

FIG. 1 is a front perspective view of a tube deploying system 100 having a cutting sheath slot 115 that faces in a first direction according to an embodiment. FIG. 2 is back perspective view of tube deploying system 100 but with a cutting sheath slot 115 facing in an opposing second direction according to an embodiment. FIG. 3 is a right side view of FIG. 1, FIG. 4 is a left side view of FIG. 1, FIG. 5 is a front view of FIG. 1, FIG. 6 is a back view of FIG. 1, FIG. 7 is a top view of FIG. 1, FIG. 8 is a bottom view of FIG. 1 and FIG. 9 is an exploded view of FIG. 1. Tube deploying system 100 includes a nose assembly 102 coupled to a handle 104 and a pull mechanism 106 that partially protrudes from handle 104 as well as is partially housed within the interior of handle 104.

Figure 10:
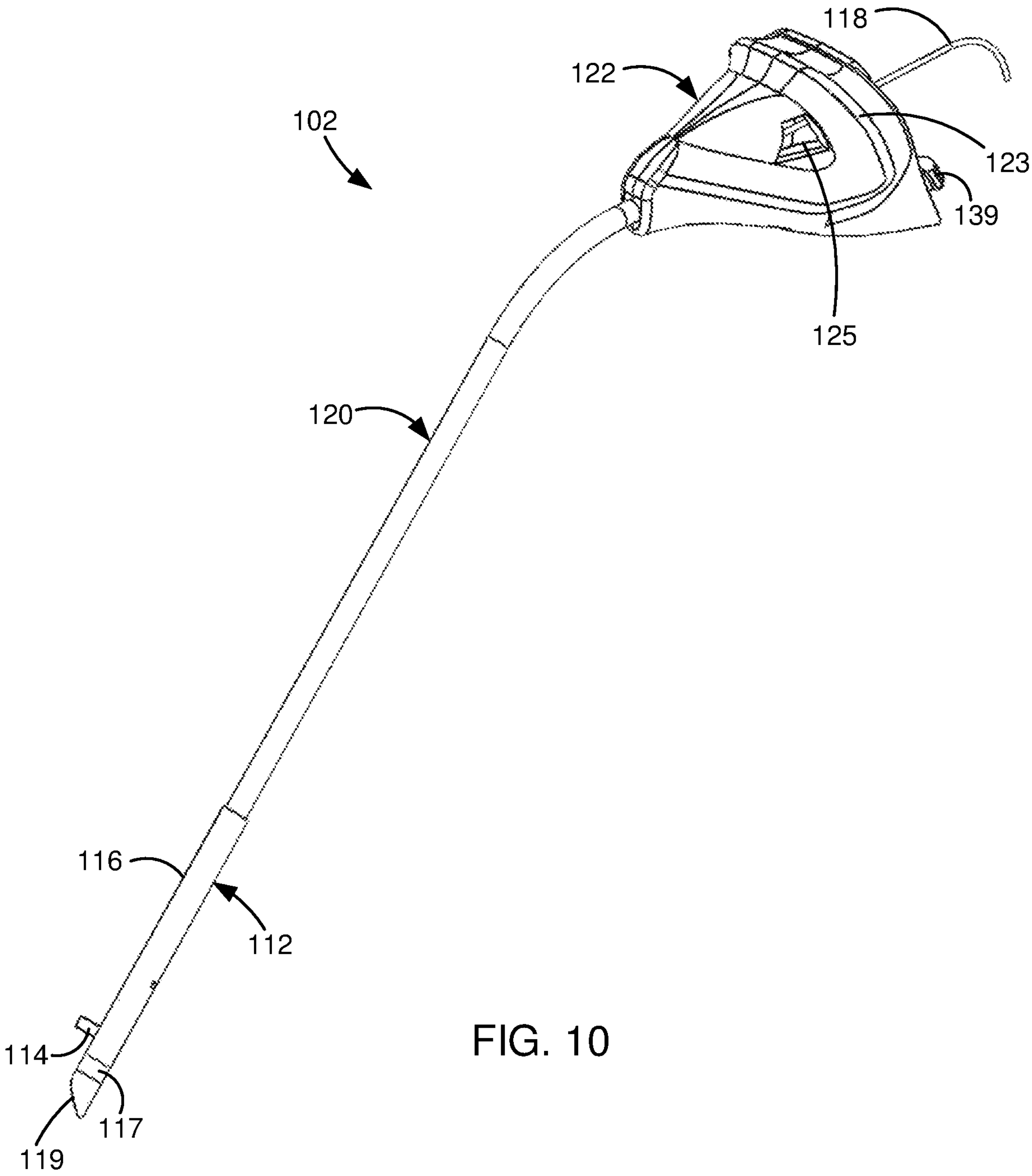
FIG. 10 is front perspective view of the nose assembly of FIGS. 1 and 3-9.
Figure 11:
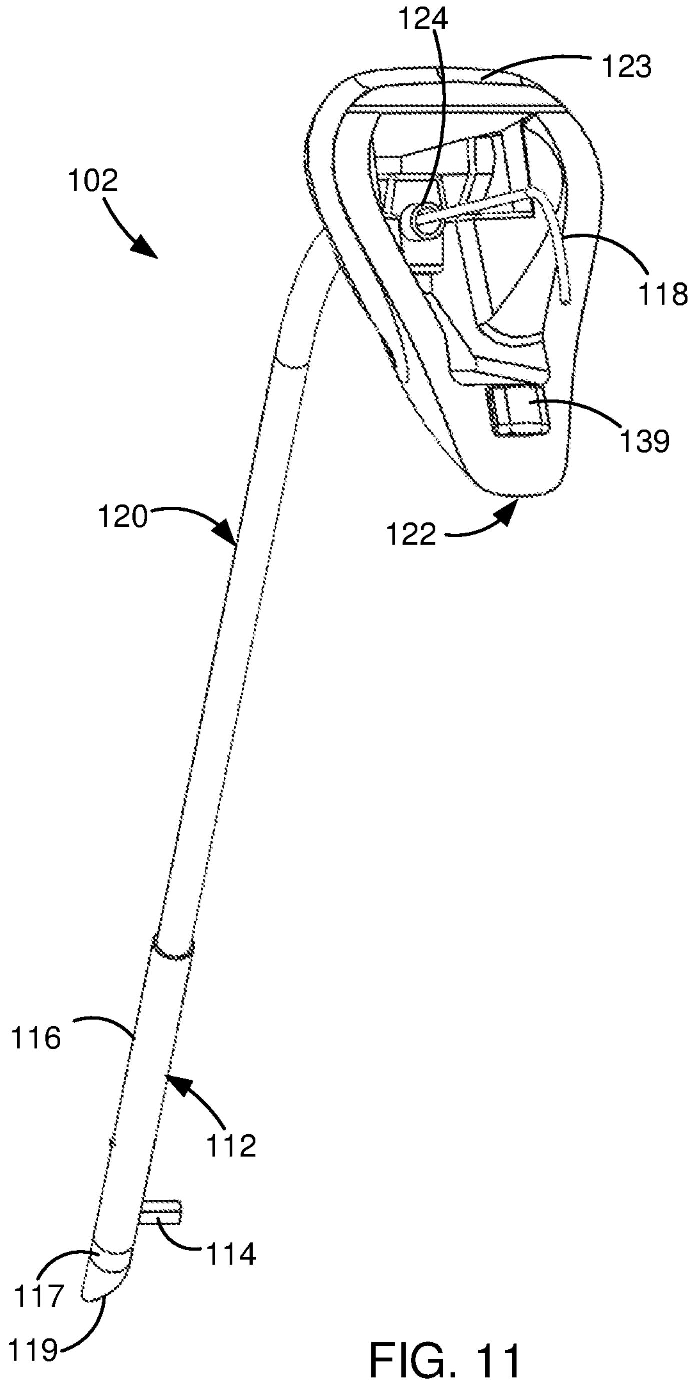
FIG. 11 is a back perspective view of FIG. 10.
Figure 12:
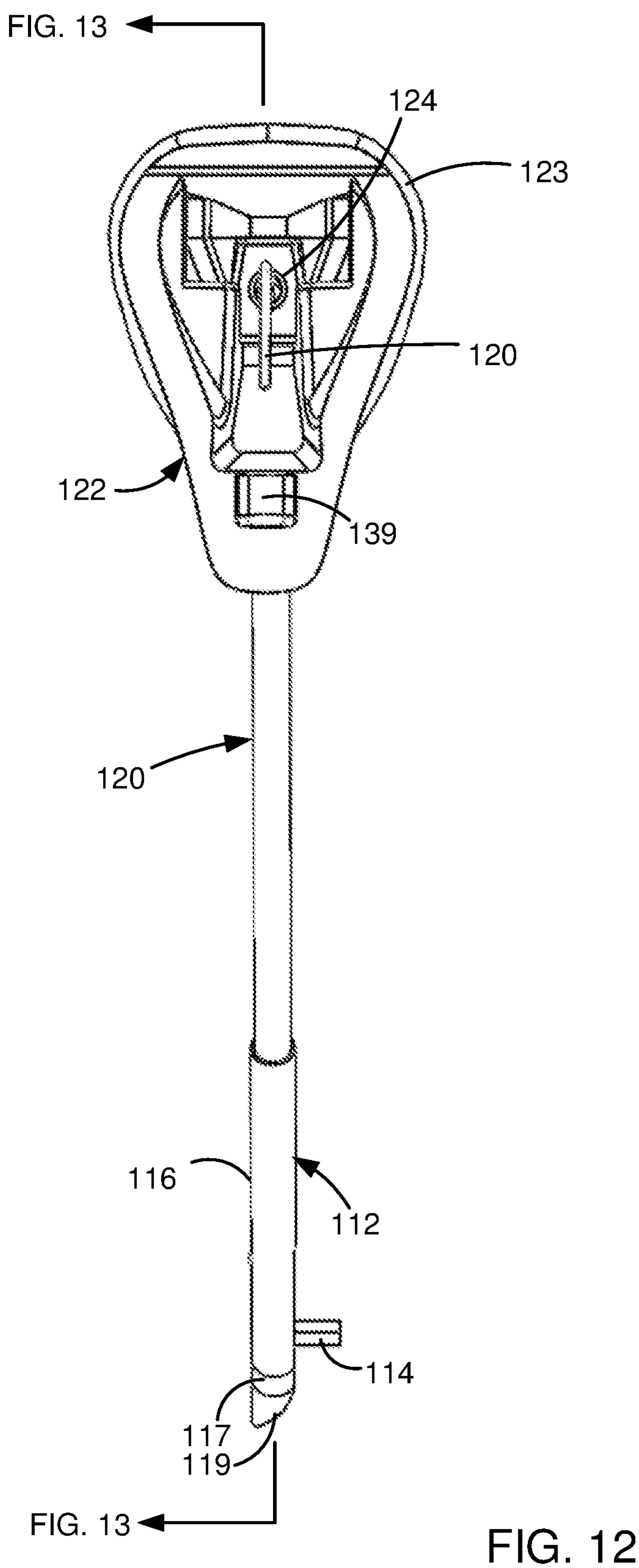
FIG. 12 is a back view of FIGS. 10 and 11.

FIG. 10 is front perspective view, FIG. 11 is a back perspective view and FIG. 12 is a back view of nose assembly 102. Nose assembly 102 includes a nose portion 122, an elongated portion 120 extending from nose portion 122 and a sheath assembly 112. In this embodiment, elongated portion 120 is a hollow positioning rod and sheath assembly 112 includes a hollow cutting sheath 116 having a distal cutting edge 119. In the illustrated embodiment, distal cutting edge 119 includes a beveled cutting edge. Portions of the hollow cutting sheath 116 surround a distal end 126 (FIG. 13) of elongated portion 120. Hollow cutting sheath 116 also at least partially houses a tube 114 configured to be placed in or deployed across a membrane of a patient.

Figure 13:
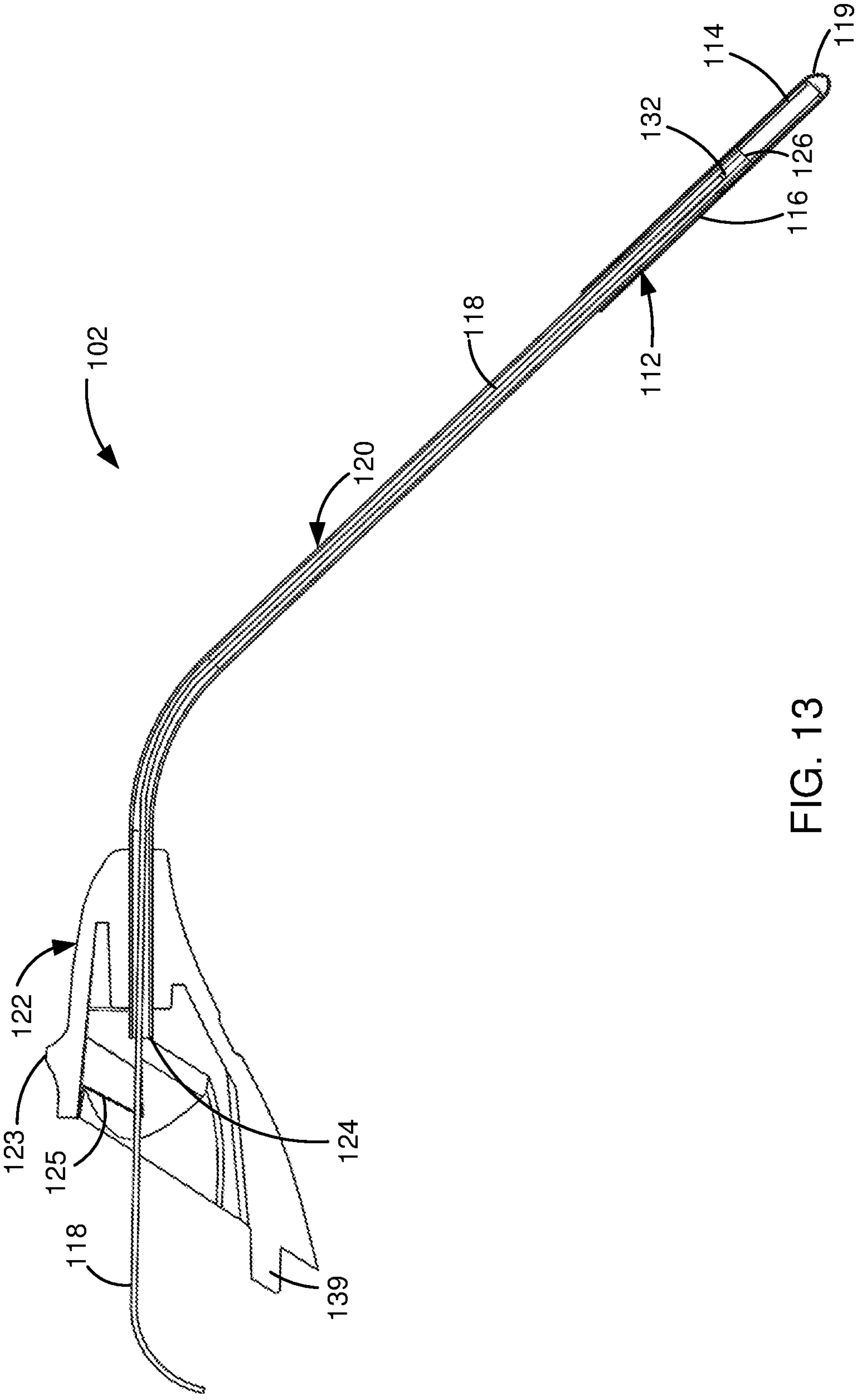
FIG. 13 is a section view taken through the section line indicated in FIG. 12.

FIG. 13 is a section view taken through the section line indicated in FIG. 12. In the embodiments illustrated in FIGS. 1-13, nose portion 122 is overmolded at or nearer to a proximal end 124 (FIGS. 11, 12 and 13) of positioning rod 120. Positioning rod 120 includes a slot 128 (FIG. 9) that extends from distal end 126 of positioning rod 120 to a terminating end 129 of slot 128. Terminating end 129 is located between distal end 126 of positioning rod 120 and proximal end 124, which is overmolded by nose 122.

An actuation member 118 (FIGS. 9 and 13) having a distal end 132 (FIG. 13) is coupled to cutting sheath 116, extends internally within cutting sheath 116, extends through slot 128 in positioning rod 120 and extends internal to and along positioning rod 120 into nose portion 122. Tube 114 is at least partially surrounded by cutting sheath 116 while a portion of tube 114 protrudes through slot 115 in cutting sheath 116. The portion of tube 114 that protrudes through slot 115 provides a visualization tab to the clinician placing the tube in a membrane of a patient.

As illustrated in FIG. 9, handle 104 includes a first side housing 130 and a second side housing 132. Each of first side housing 130 and second side housing 132 includes an area 135 (FIGS. 2, 3, 9) and an area 137 (FIGS. 1 and 4), respectively, of molded texture. This molded texture is different from other surfaces of first and second side housings 130 and 132 to enable haptic differentiation. The molded texture of areas 135 and 137 may be in the shape of undercuts and scoops to provide haptic feedback for correct finger positioning. The molded texture may also provide points of resistance to prevent system 100 from sliding forward or backward in the clinician's hand during use. Together, first side housing 130 and second side housing 132 couple together to internally house at least a portion of pull mechanism 106. In one embodiment, handle 104 is connected to nose portion 122 with snap-on members 131 and 133 (FIG. 9). Snap-on members 131 and 133 prevent relative left to right and right to left twisting. An interlock element 139 (FIGS. 9-13) reduces the chance of the nose twisting up when a downward force to make an incision is applied by the clinician. Snap-on members 131 and 133 and interlock element 139 combine to form a multipoint stable attachment between nose assembly 102 and handle 104. It should be realized that snap-on members 131 and 133 could be interlock elements and interlock element 139 could be a snap-on member. In addition, handle 104 is configured to receive removable locking pin 108 and removable assembly clip 110. Removable assembly clip 110 allows for the assembly of first and second side housings 130 and 132 as well as the disassembly of first and second side housings 130 and 132. Pull mechanism 106, removable locking pin 108 and removable assembly clip 110 will be discussed in more detail below.

Figure 14:
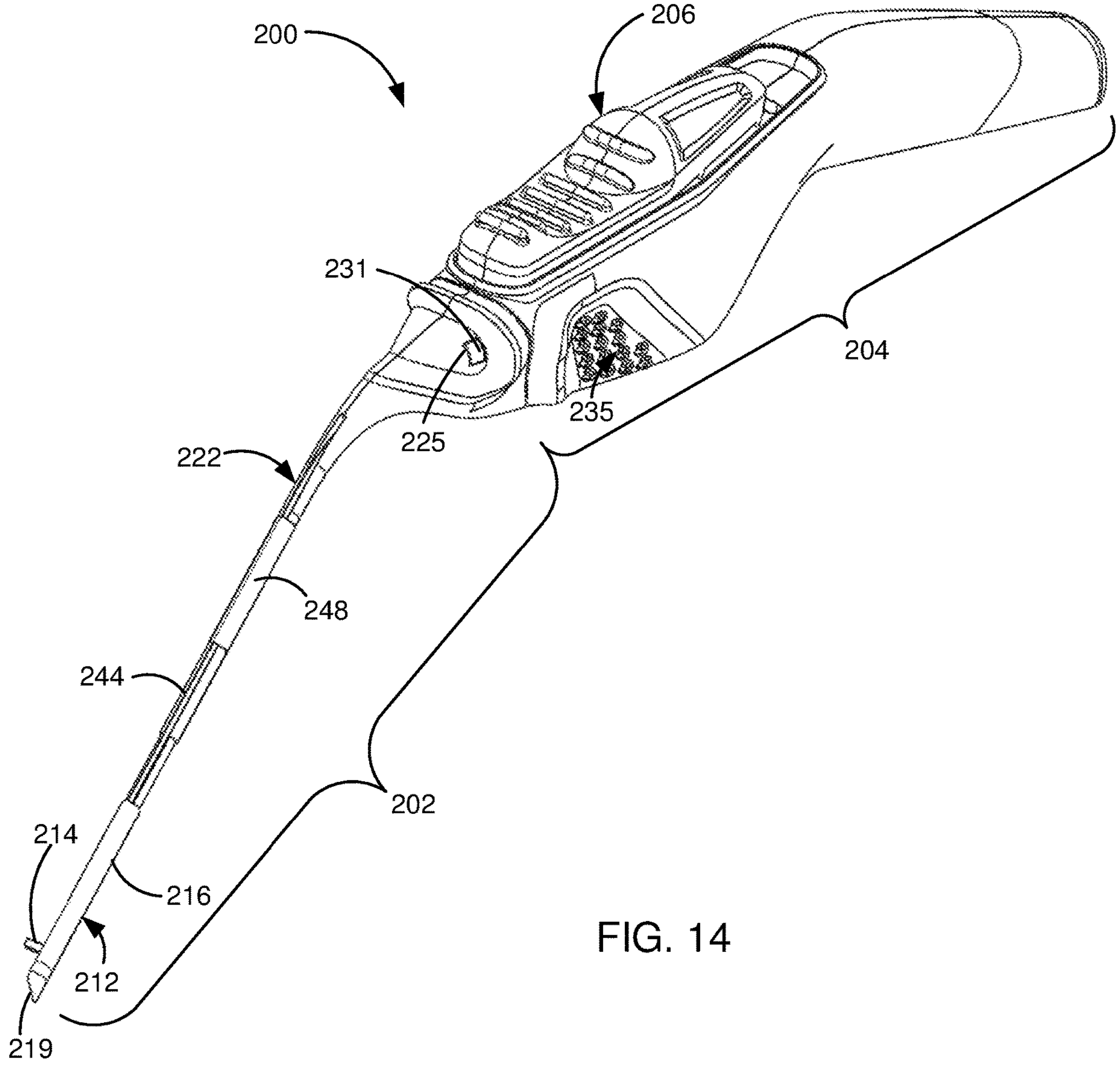
FIG. 14 is a front perspective view of another tube deploying system having a cutting sheath slot facing in a first direction according to an embodiment.
Figure 15:
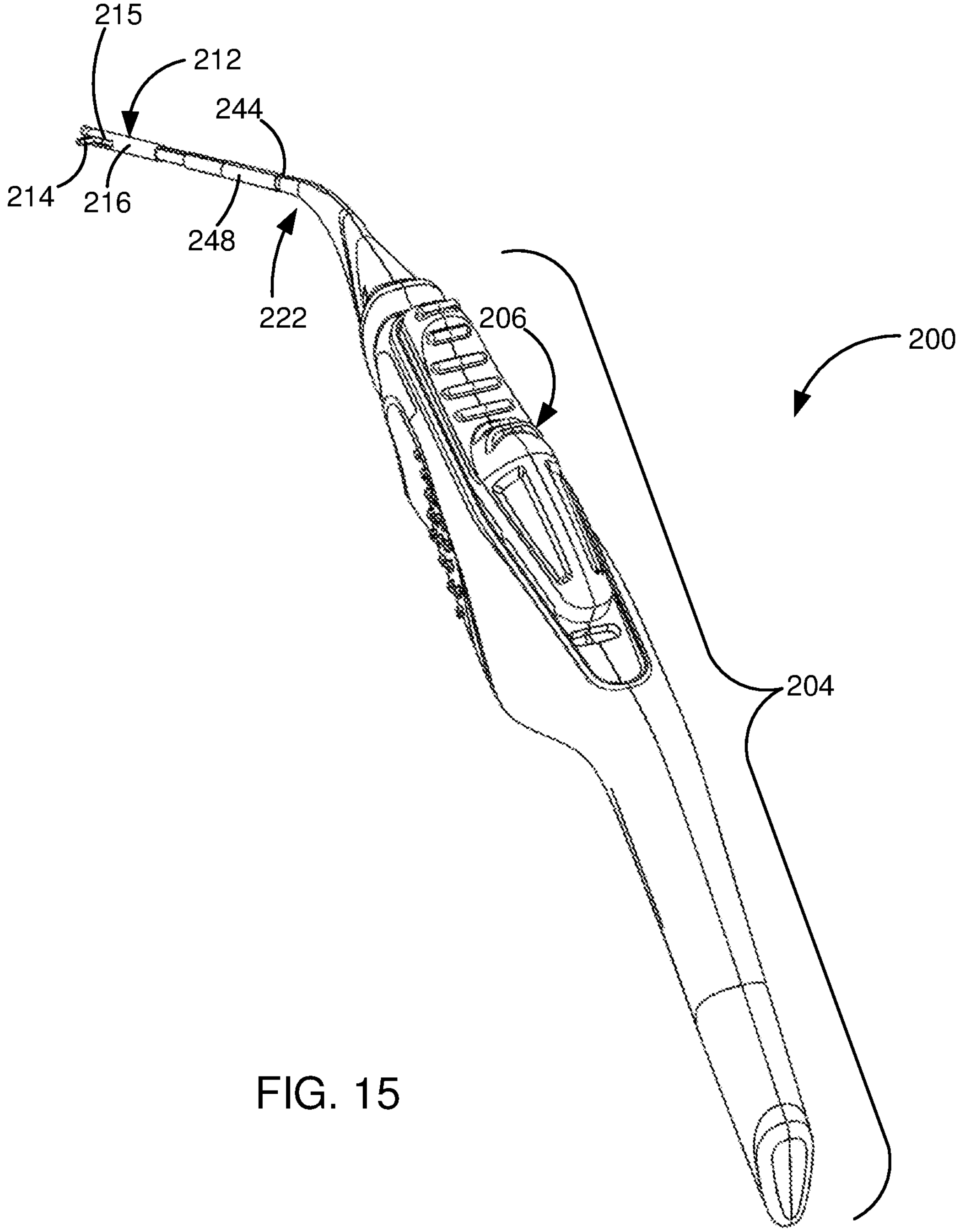
FIG. 15 is a back perspective view of the tube deploying system illustrated in FIG. 14 but with a cutting sheath slot facing in a second direction according to an embodiment.
Figure 16:
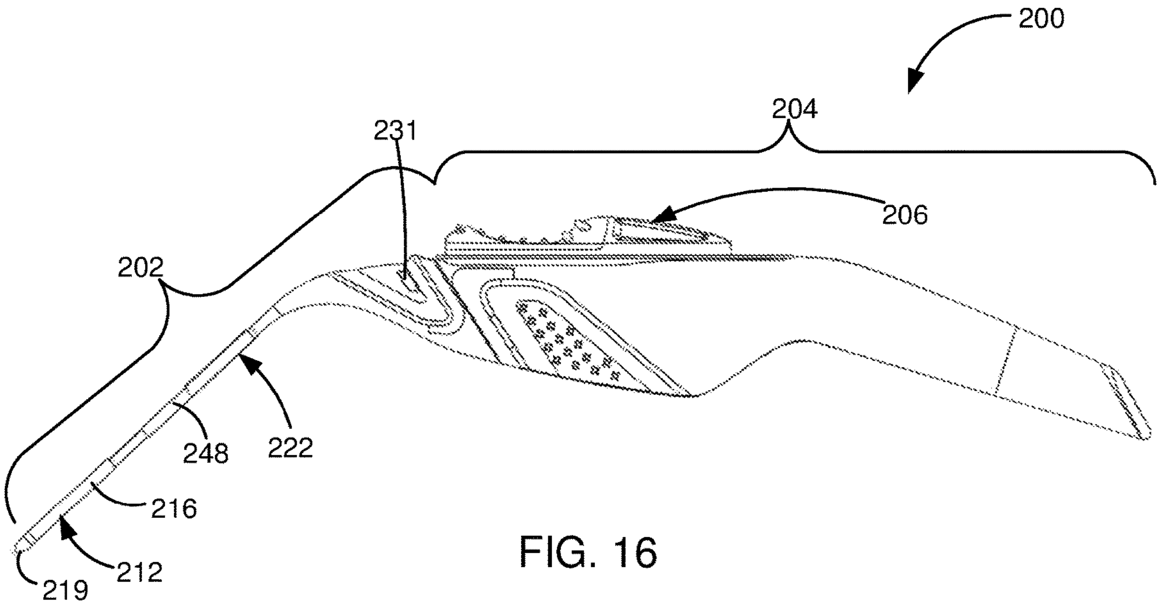
FIG. 16 is a right side view of FIG. 14.
Figure 17:
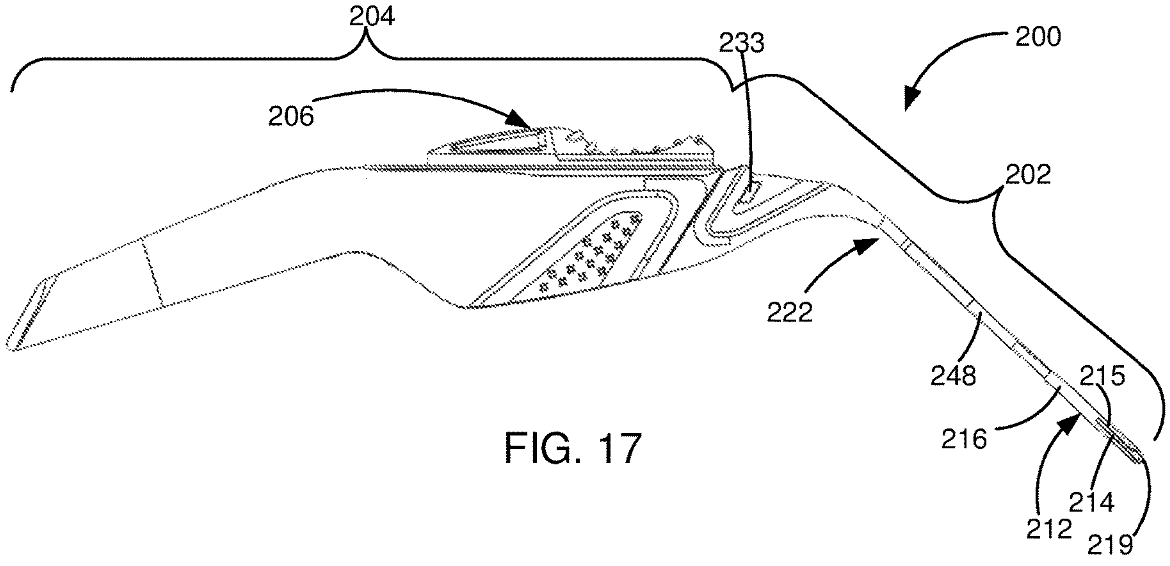
FIG. 17 is a left side view of FIG. 14.
Figure 18:
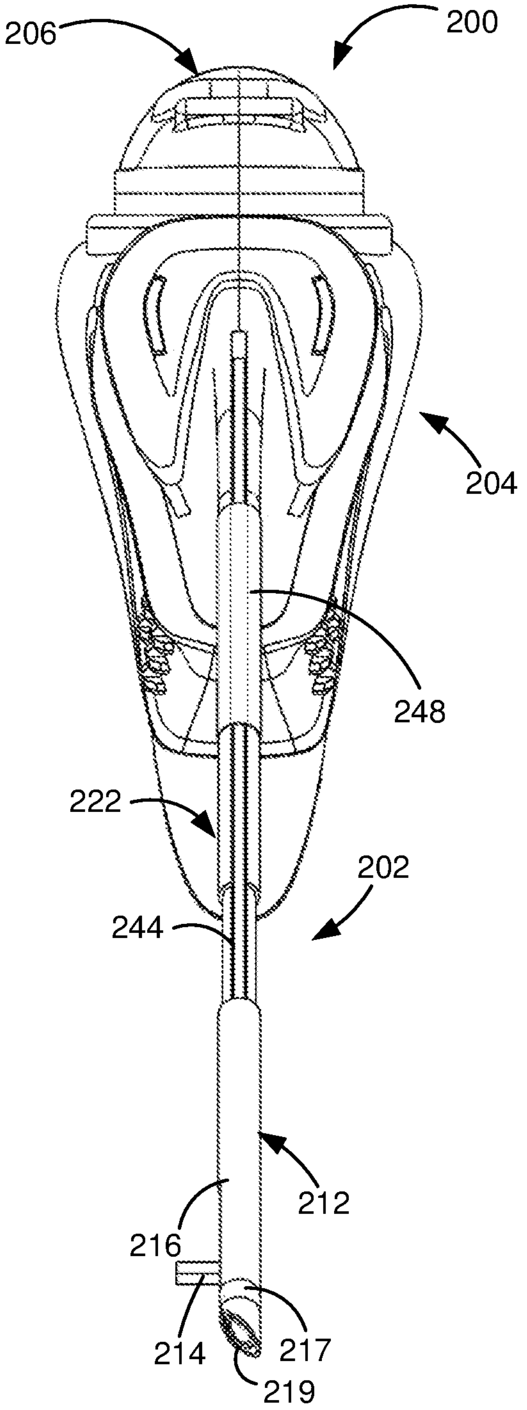
FIG. 18 is a front view of FIG. 14.
Figure 19:
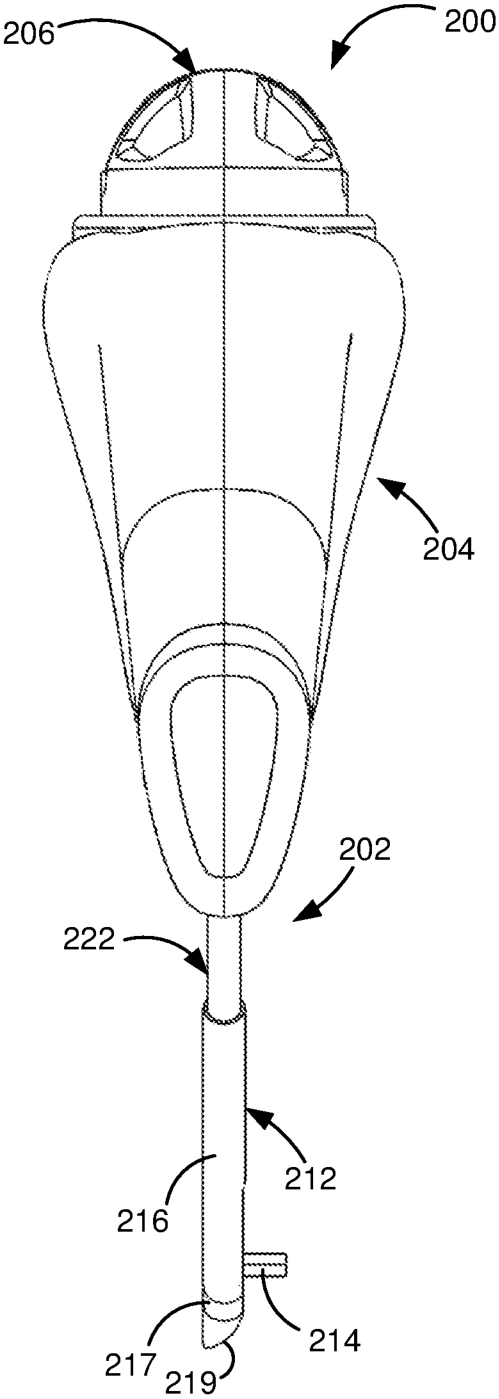
FIG. 19 is a back view of FIG. 14.
Figure 20:
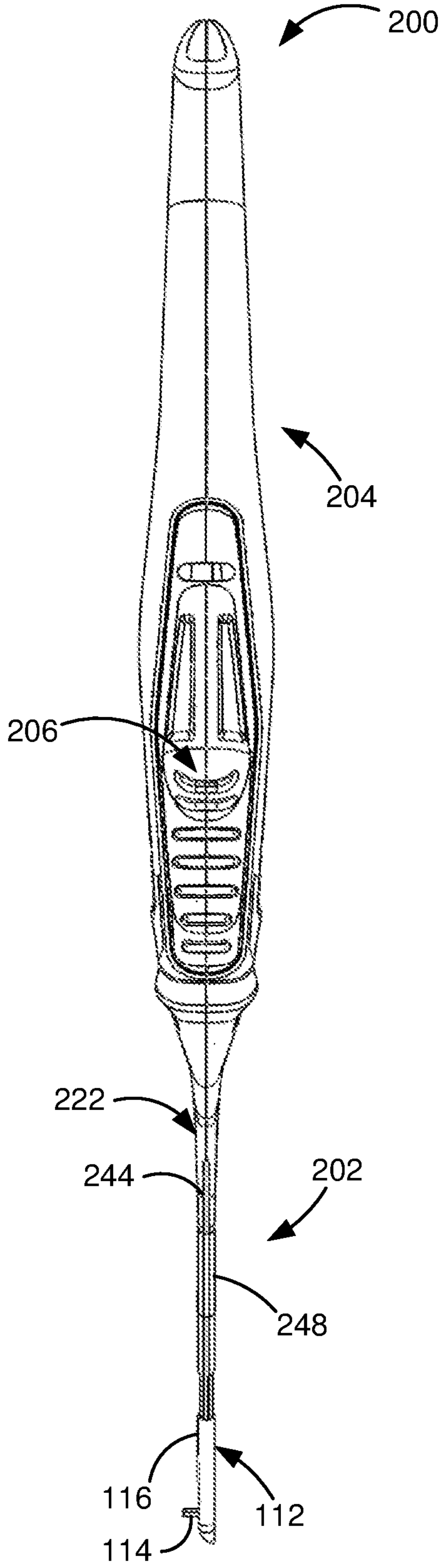
FIG. 20 is a top view of FIG. 14.
Figure 21:
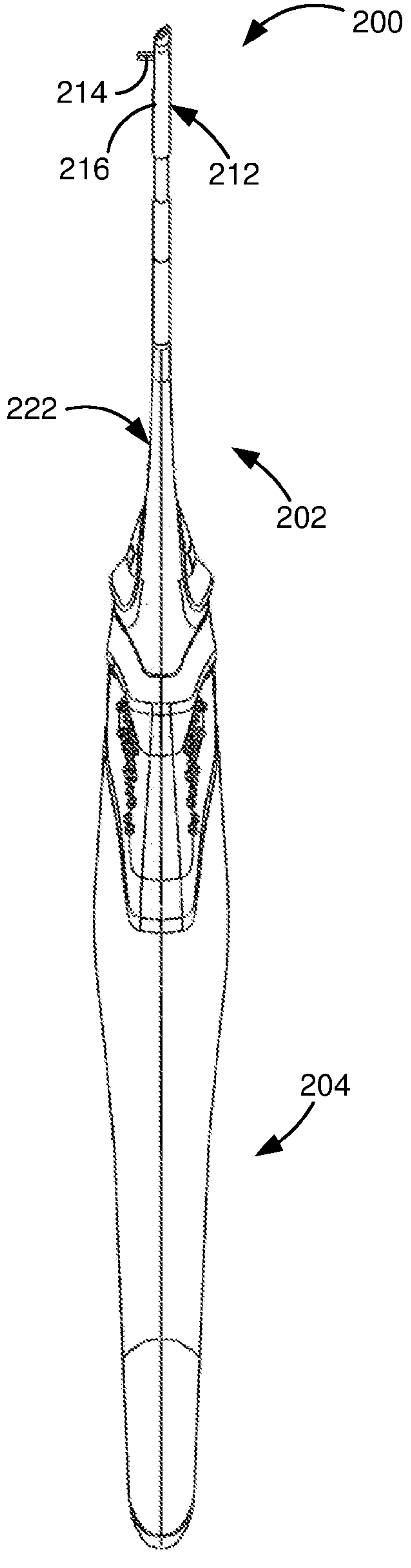
FIG. 21 is a bottom view of FIG. 14.
Figure 22:
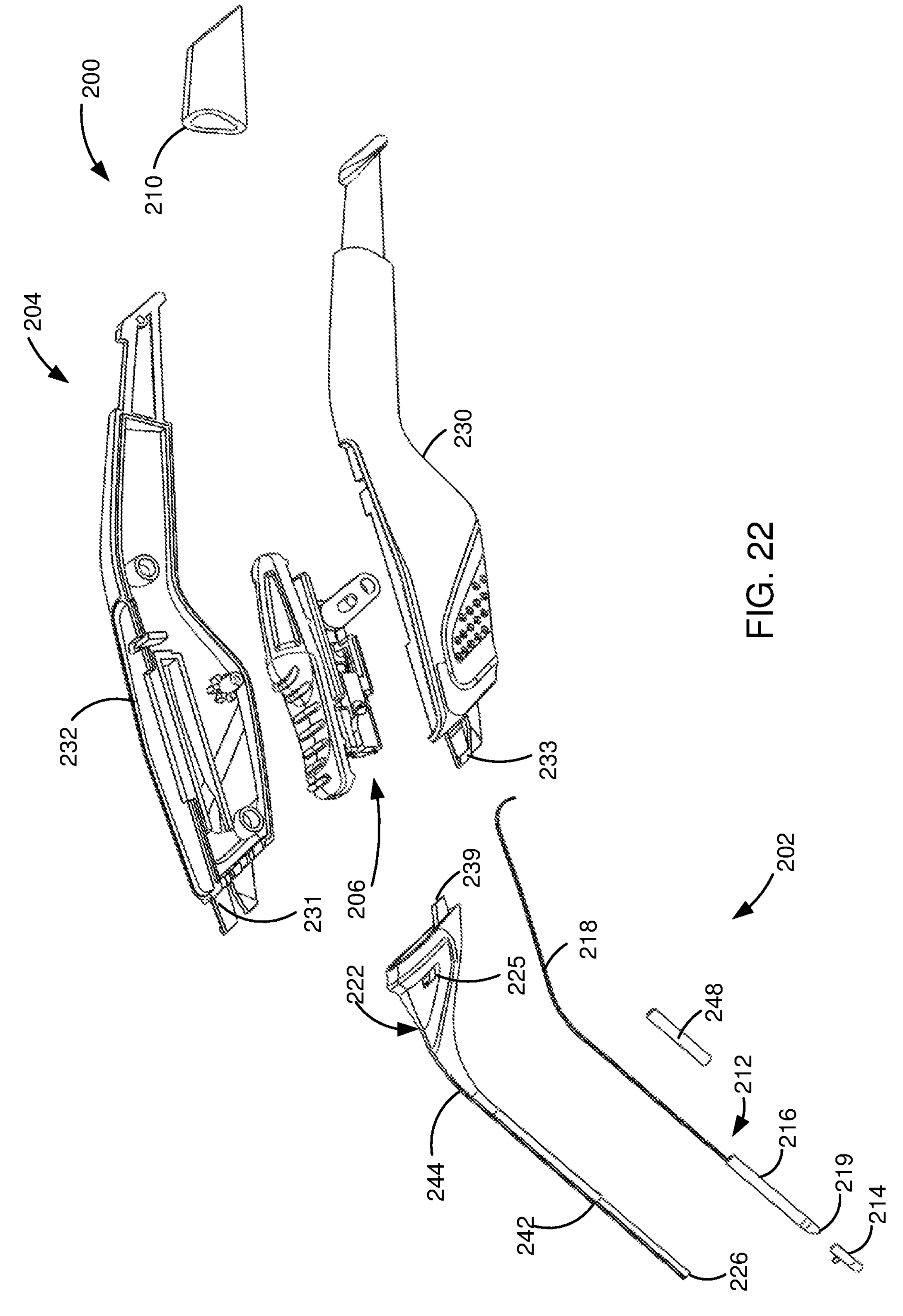
FIG. 22 is an exploded view of FIG. 14.

FIG. 14 is a front perspective view of tube deploying system 200 having a cutting sheath slot that faces in a first direction according to an embodiment. FIG. 15 is a back perspective view of tube deploying system 200 but with a cutting sheath slot 215 facing in a second direction that opposes the first direction according to an embodiment. FIG. 16 is a right side view, FIG. 17 is a left side view, FIG. 18 is a front view, FIG. 19 is a back view, FIG. 20 is a top view, FIG. 21 is a bottom view and FIG. 22 is an exploded view of tube deploying system 200. System 200 includes a nose assembly 202 coupled to the a handle 204 Pull mechanism 206 of system 200 partially protrudes from handle 204 and is at least partially housed within the interior of handle 204. Handle 204 is connected to nose assembly 202 with snap-on members 231 and 233 (FIG. 22). Snap-on members 231 and 233 prevent relative left to right and right to left twisting. Interlock element 239 (FIGS. 22-27) reduces the chance of the nose twisting up when a downward force to make an incision is applied by the clinician. Snap-on members 231 and 233 and interlock element 239 combine to form a multipoint stable attachment between nose assembly 202 and handle 204. It should be realized that snap-on members 231 and 233 could be interlock elements and interlock element 239 could be a snap-on member. Handle 204 of system 200, like handle 104 of system 100, may be configured to receive a removable locking pin (not shown) and removable assembly clip 210. Removable assembly clip 210 allows for the assembly of first and second side housings 230 and 232 of handle 204 as well as the disassembly of first and second side housings 230 and 232. In one embodiment, clip 210 may be an elastomeric material that expands to be placed over the proximal end of first and second side housings 230 and 232 and contracts to hold first and second side housings 230 and 232 together. However, clip 210 may be a resilient removable clip, or system 200 may not include a clip and alternatively include a feature that allows first and second side housings 230 and 232 to be pushed together. Pull mechanism 206, as previously mentioned, will be discussed in more detail below.

Figure 23:
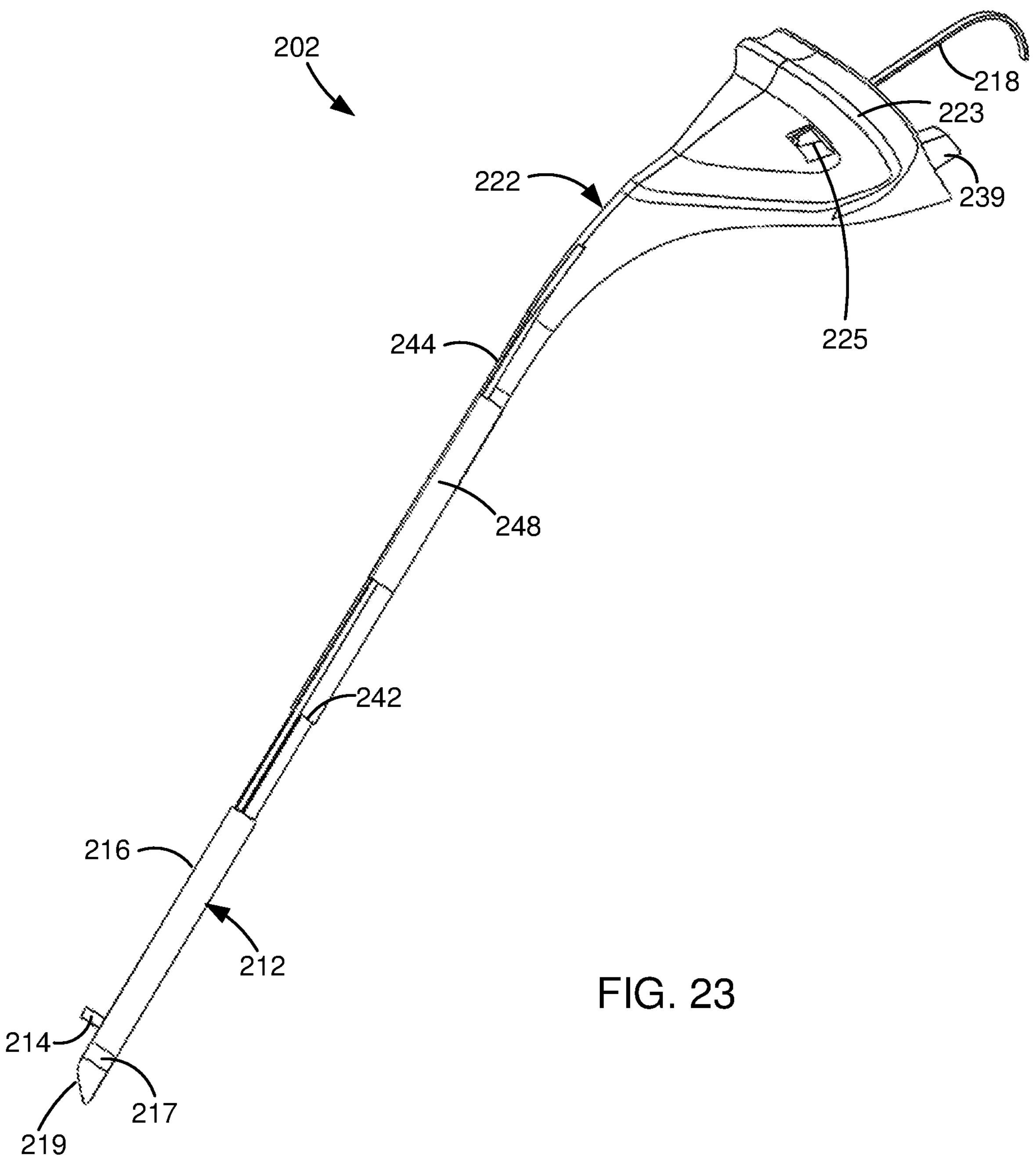
FIG. 23 is a front perspective view of the nose assembly of FIGS. 14 and 16-22.
Figure 24:
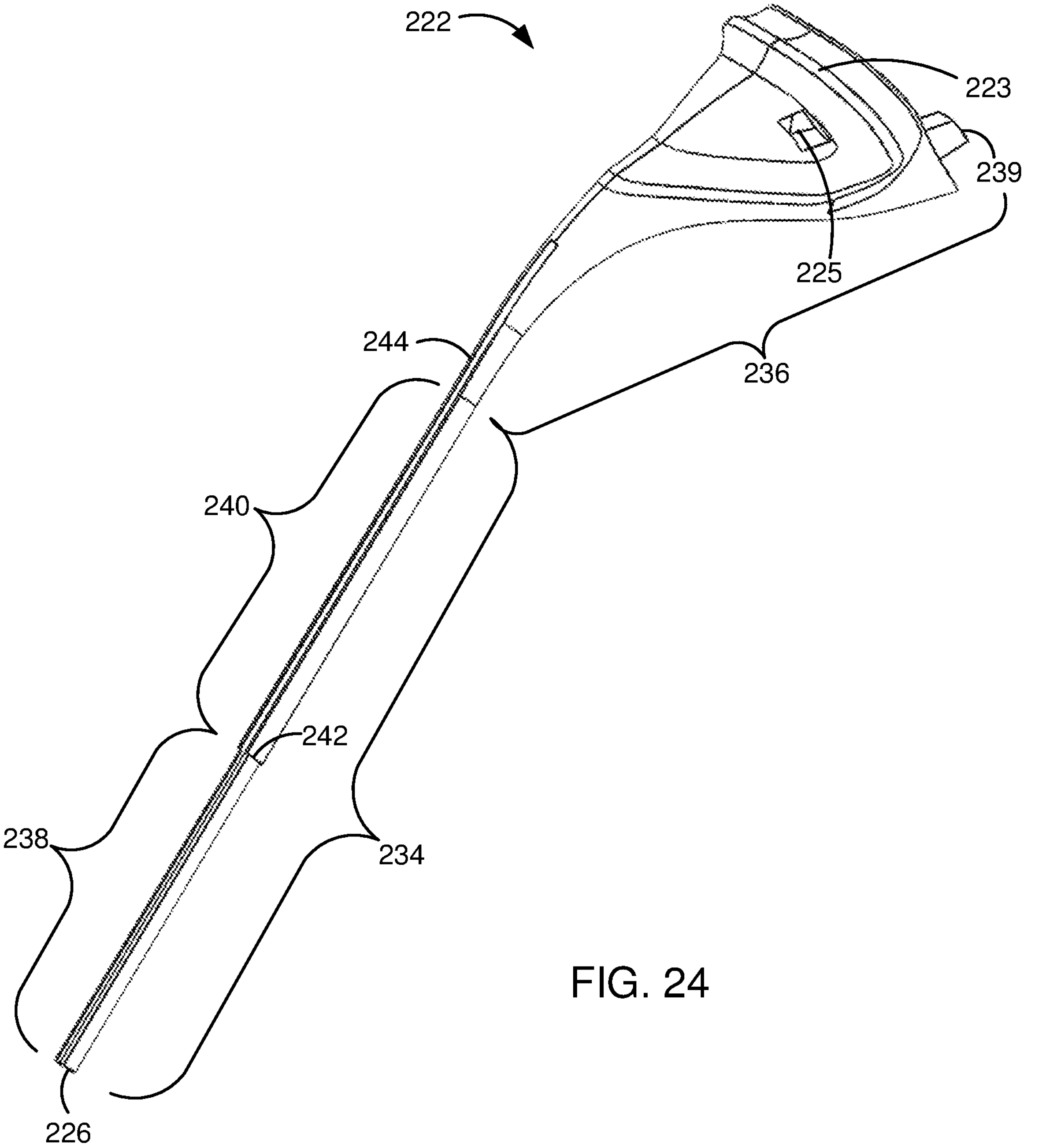
FIG. 24 is a front perspective view of the nose of the nose assembly of FIG. 23.
Figure 25:
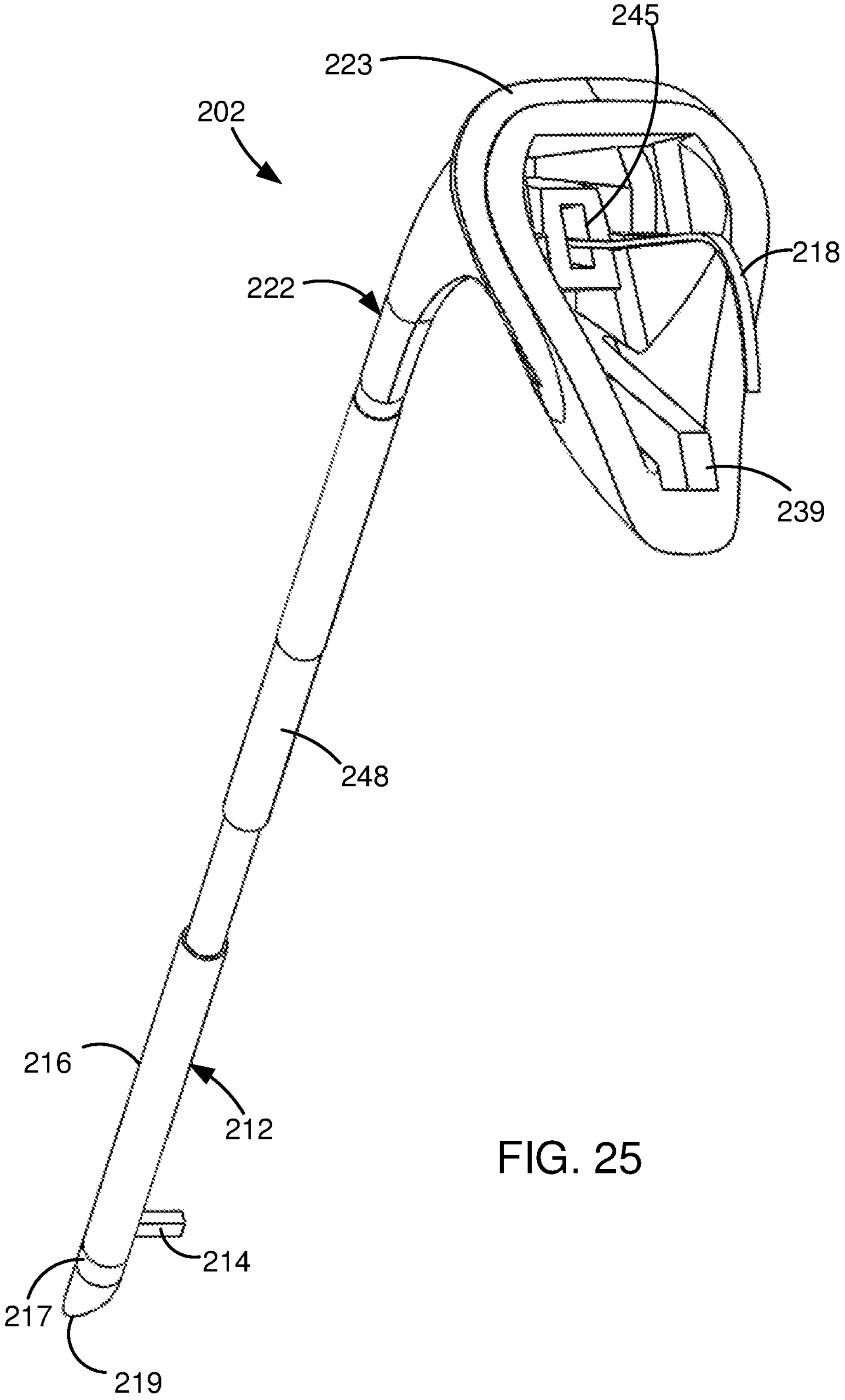
FIG. 25 is a back perspective view of the nose assembly of FIG. 23.
Figure 26:
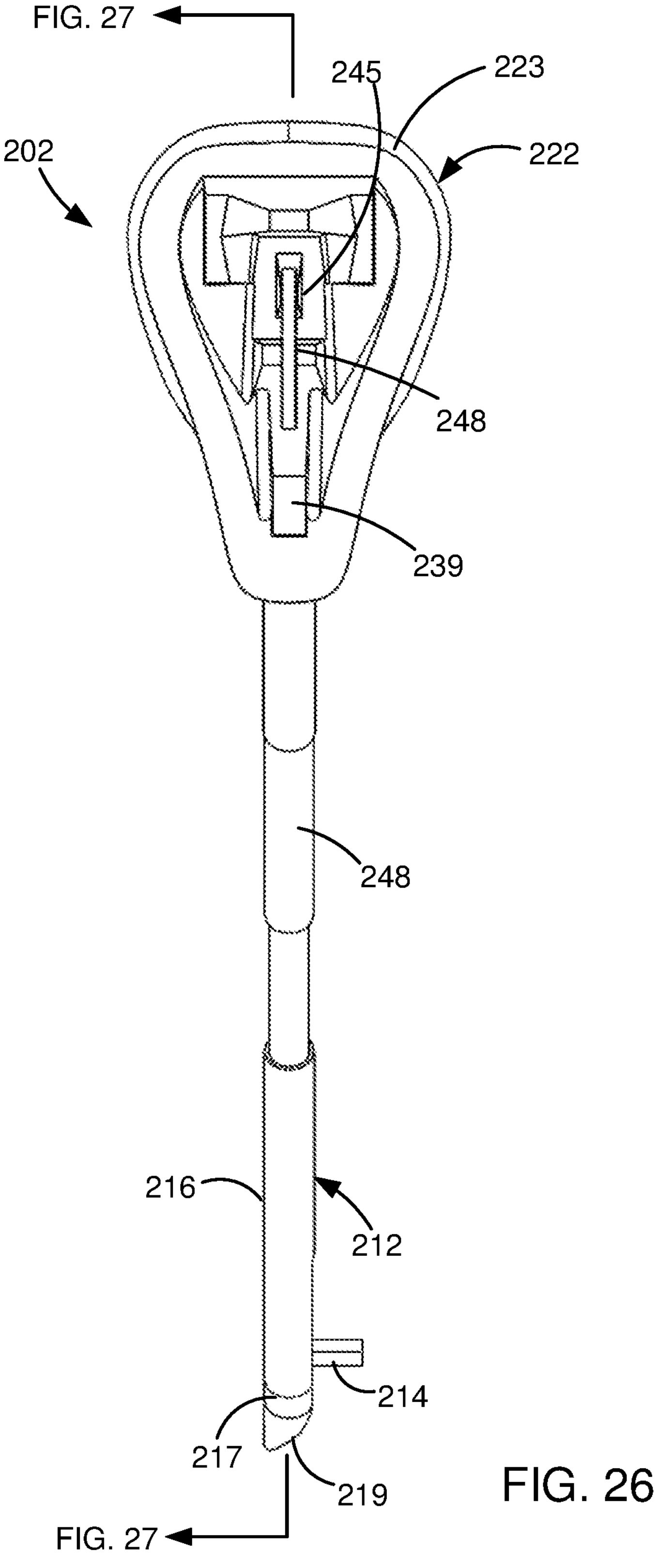
FIG. 26 is a back view of the nose assembly of FIG. 23.
Figure 27:
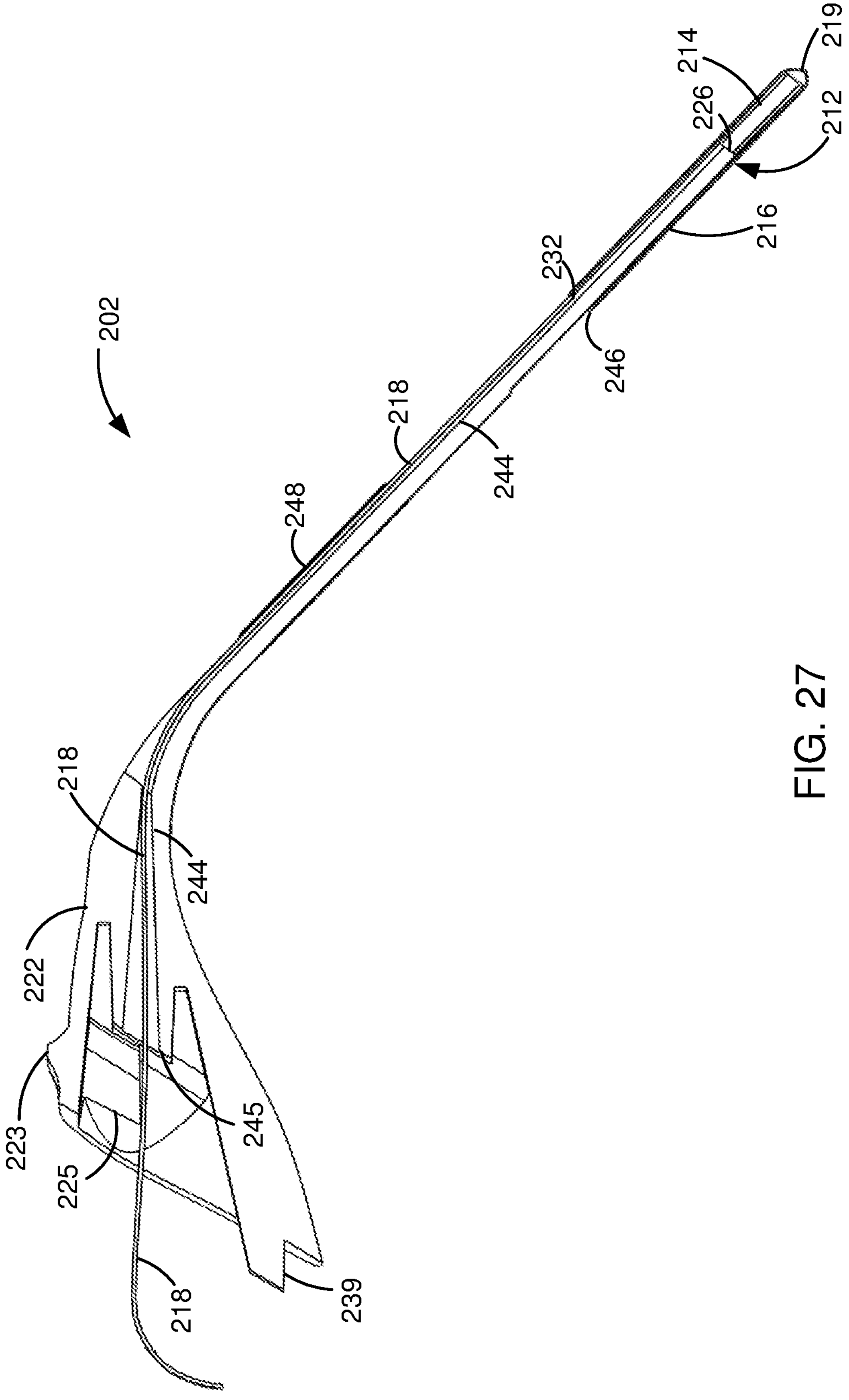
FIG. 27 is a section view taken through the section line of FIG. 26.

FIG. 23 is a front perspective view of nose assembly 202. FIG. 24 is a front perspective view of a nose 222 of nose assembly 202. FIG. 25 is a back perspective view and FIG. 26 is a back view of nose assembly 202. FIG. 27 is a section view taken through the section line in FIG. 26. Nose assembly 202 includes a nose 222 and a sheath assembly 212. Nose 222 has an elongated portion 234 (FIG. 24) and a nose portion 236 (FIG. 24). Elongated portion 234 extends distally from nose portion 236. Sheath assembly 212 includes a hollow cutting sheath 216 and a tube 214 at least partially surrounded by hollow cutting sheath 216 and configured to be placed in or deployed across a membrane of a patient.

In the embodiments illustrated in FIGS. 14-27, elongated portion 234 and nose portion 236 of nose 222 are made of a single molded part and hollow cutting sheath 216 surrounds a distal end 226 of elongated portion 234 as well as surrounds a section of elongated portion 234 of nose 222. Elongated portion 234 includes two different widths. A first section 238 of elongated portion 234 includes a first width that extends from distal end 226 to a travel stop 242. First section 238 provides a zone for the travel of cutting sheath 216. A second section 240 of elongated portion 234 includes a second width that extends from travel stop 242 to where elongated portion 234 ends. In another embodiment, second width of portion 234 may be a variable width. For example, a width that gets larger towards the proximal end to add strength. The change in width from the first width in first section 238 to the second width in second section 240 provides the stop for hollow cutting sheath 216. Second section 240 provides a zone where an external wrap, such as shrink tubing, can be applied. Travel stop 242 will be described in more detail upon discussion of the operation of tube deploying system 200. In the molded embodiments illustrated in FIGS. 14-22, nose 222 includes a channel 244 that extends from distal end 226 of elongated portion 234 to the back of nose portion 236. The portion of channel 244 that extends in elongated portion 234 is an open channel, slot or groove that acts as a guide for an actuation member 218. Channel 244 extends to distal end 226 of elongated portion 234 to allow for clearance of a weld joint, such as a butt joint, between 141*b*

218 and cutting sheath 216. The portion of channel 244 that extends in nose portion 236 is an enclosed channel or passage having an outlet 245 (FIGS. 25-27). Actuation member 218 includes a distal end 232 (FIG. 27) that couples to a proximal end 246 (FIG. 27) of cutting sheath 216, extends in and through the portion of channel 244 that is the open channel or slot in elongated portion 234 of nose 222 and continues in the portion of channel 244 that is the enclosed channel in nose portion 236 of nose 222. In one embodiment of system 200, channel 244 allows actuation member 218 to be a rectangular or flat wire (as opposed to a round wire, like the round wire actuation member 118 of system 100) so as to maximize wire cross section while minimizing the amount of cross section of nose 222 that must be removed to create the passageway for actuation member 218, which allows nose 222 to retain structural integrity. In another embodiment, it is possible that channel 244 is only deep enough to act as a guide and a portion of actuation member 244 extends above or outside of channel 244. Tube 214 is at least partially surrounded by cutting sheath 216 while a portion of tube 214 protrudes through a slot 215 in cutting sheath 216. The portion of tube 214 that protrudes through slot 215 (FIGS. 15 and 17) provides a visualization landmark to the clinician placing the tube in or deploying the tube across the membrane of a patient. External wrap 248, such as shrink wrap or similar, is wrapped around elongated portion 234 of nose 222 in second section 240 to retain actuation member 218 in the open groove of channel 244 at all times including when actuation member 218 is actuated, which will be discussed in detail below.

Figure 28:
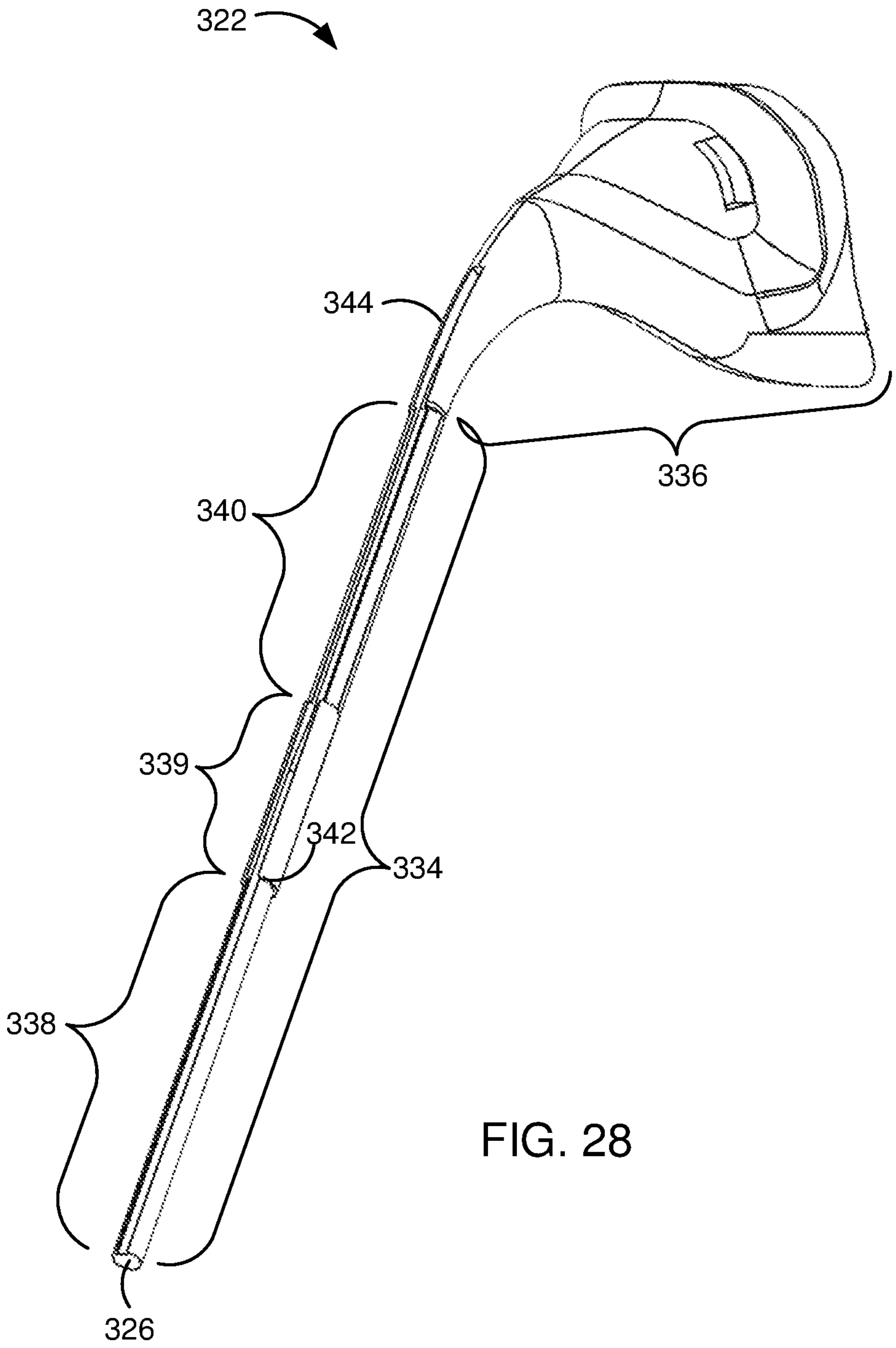
FIG. 28 is a front perspective view of a nose of another embodiment of a nose assembly.

FIG. 28 is a front perspective view of a nose 322 according to another embodiment of a nose assembly. Nose 322 is made of a single molded part and includes an elongated portion 334 and a nose portion 336. Nose 322 may be substituted for nose 222 in nose assembly 202. Elongated portion 334 extends distally from nose portion 336. Hollow cutting sheath 216 may be configured to surround a distal end 326 of elongated portion 334 as well as is configured to surround a section of elongated portion 334 as was discussed in the figures related to nose 222. Elongated portion 334 includes three different widths. A first section 338 of elongated portion 334 includes a first width that extends from distal end 326 to a travel stop 342. A second section 339 of elongated portion 334 includes a second width that extends from travel stop 342 to a third section 340. Third section 340 includes a third width and extends from second section 339 to where elongated portion 334 ends and nose portion 336 begins. The change in width from the first width in first section 338 to the second width in second section 339 provides travel stop 342 for a hollow cutting sheath. The change in width from the third width in third section 340 to the second width in second section 339 provides a notch for external wrap 248 placement. Such a notch keeps external wrap 248 from adding too much thickness in elongated portion 334 that might block line of sight to tube 214 during placement and deployment.

Nose 322 includes a channel 344 that extends from distal end 326 to the back of nose portion 336. The portion of channel 344 that extends in elongated portion 334 is an open channel or slot. The portion of channel 344 that extends in nose portion 336 is an enclosed channel. Channel 344 is configured to house and hold an actuation member, such as actuation member 218 that is connected to or butt welded to cutting sheath 216.

Figure 29:
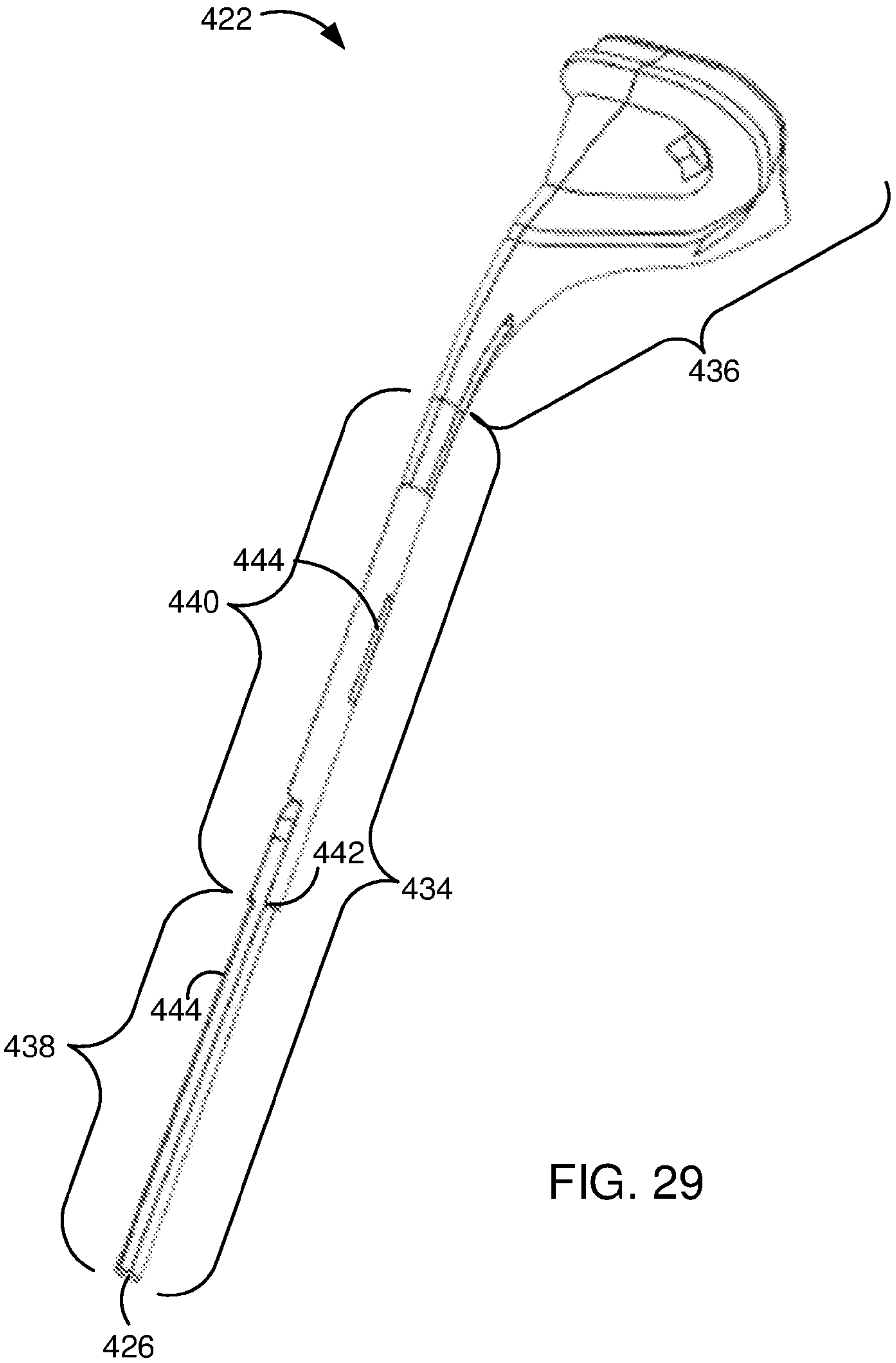
FIG. 29 is a right front perspective view of a nose according to yet another embodiment of a nose assembly.
Figure 30:
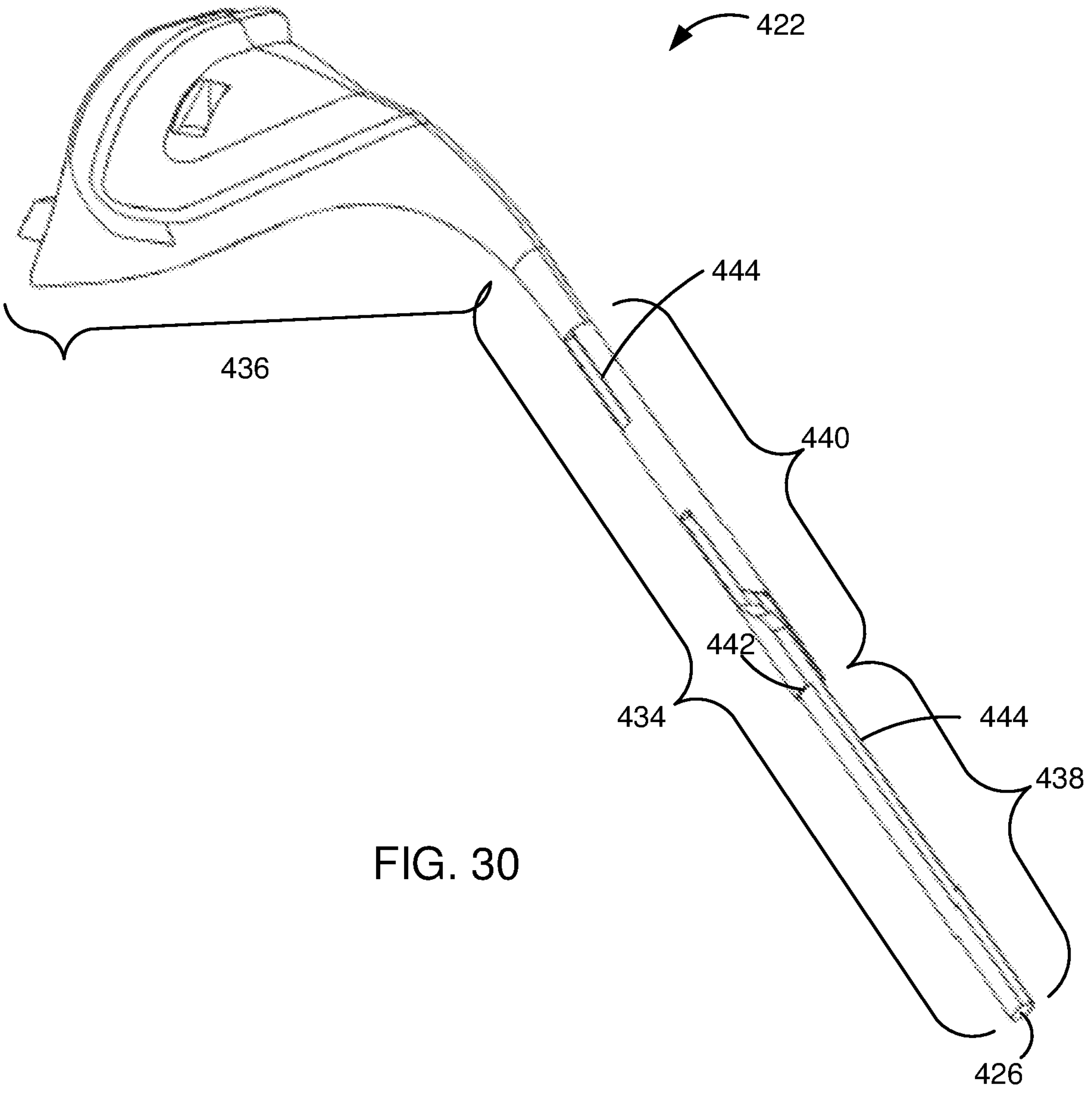
FIG. 30 is a left front perspective view of the nose of FIG. 29.
Figure 31:
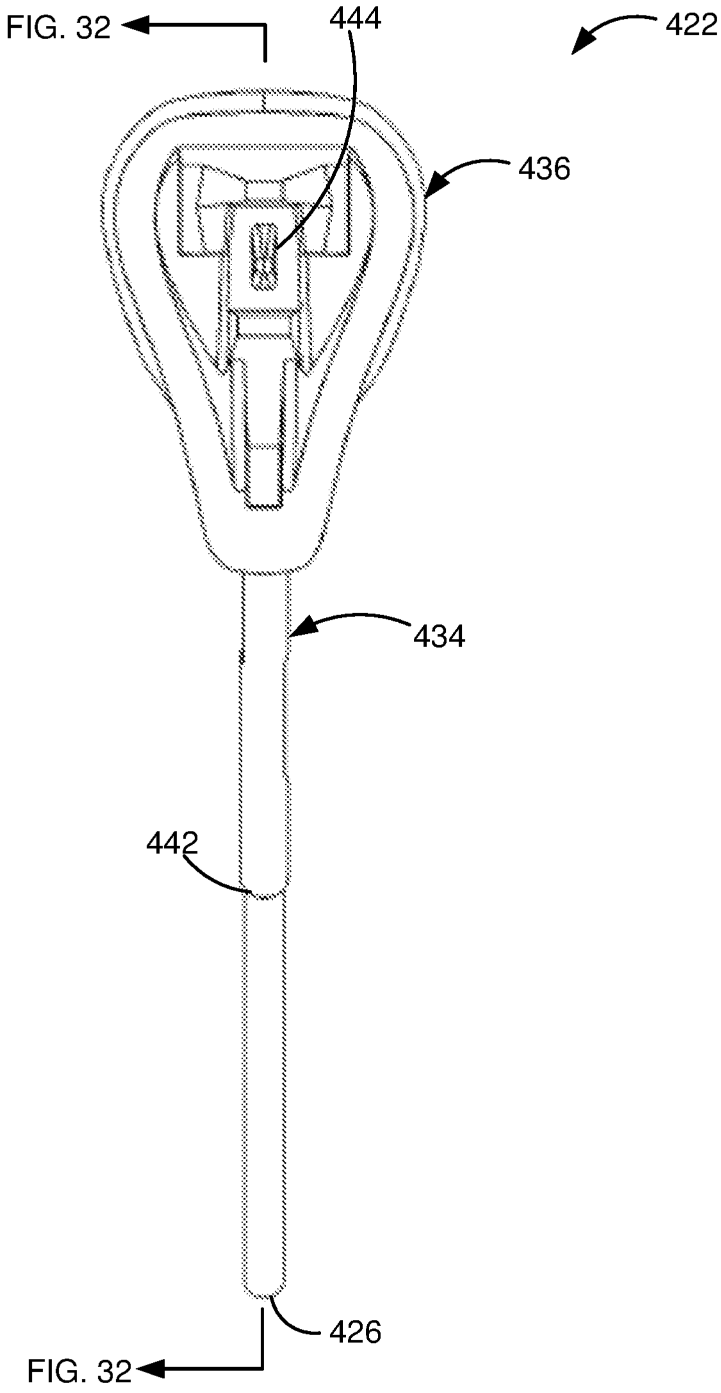
FIG. 31 is a back view of the nose of FIGS. 29 and 30.
Figure 32:
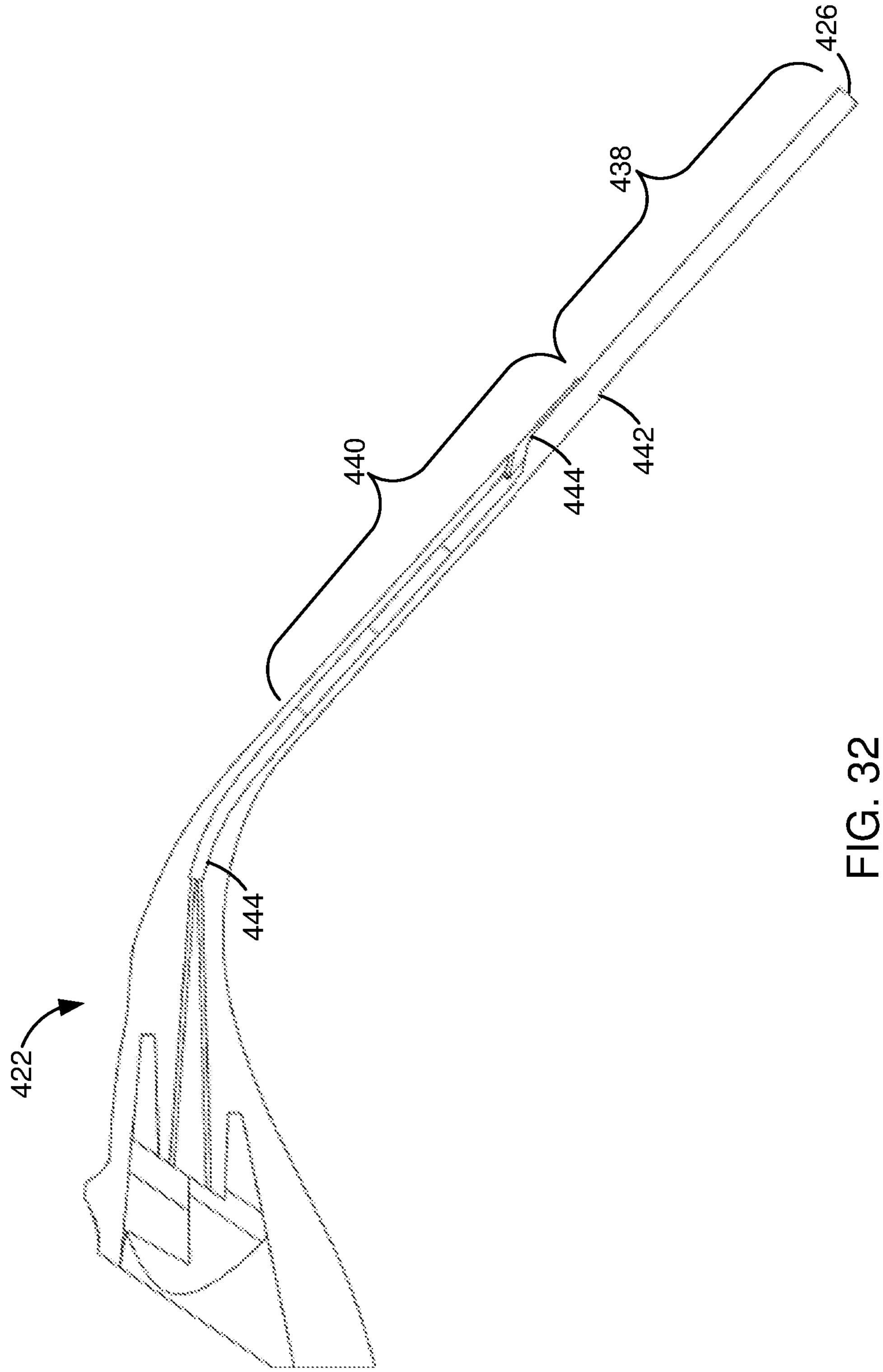
FIG. 32 is a section view taken through the section line of FIG. 31.

FIG. 29 is a right front perspective view, FIG. 30 is a left front perspective view and FIG. 31 is a back view of a nose 422 according to yet another embodiment of a nose assembly. FIG. 32 is a section view taken through the line indicated in FIG. 31. Nose 422 is made of a single molded part and includes an elongated portion 434 and a nose portion 436. Nose 422 may be substituted for nose 222 in nose assembly 202. Elongated portion 434 extends distally from nose portion 436. Hollow cutting sheath 216 may be configured to surround a distal end 426 of elongated portion 434 as well as configured to surround a section of elongated portion 434 of nose 422 as was discussed in the figures related to nose 222. Elongated portion 434 includes a first section 438 that extends from distal end 426 to a travel stop 442. A second section 440 extends from travel stop 442 to where elongated portion 434 ends and nose portion 436 begins.

Nose 422 includes a channel 444 that extends from distal end 426 to the back of nose portion 436. The portion of channel 444 that extends in first section 438 of elongated portion 434 is a straight open channel or slot. At second section 440, channel 444 includes a side pass through into the open channel or slot of first section 438. This arrangement supports an actuation member, such as actuation member 218, in channel 444 without requiring any additional element to constrain the actuation member to the channel, such as external wrap 248. The portion of channel 444 that extends in nose portion 436 is an enclosed channel. As previously described in other embodiments, channel 444 is configured to house and hold an actuation member, such as actuation member 218, which is connected to or butt welded to cutting sheath 216.

Figure 33:
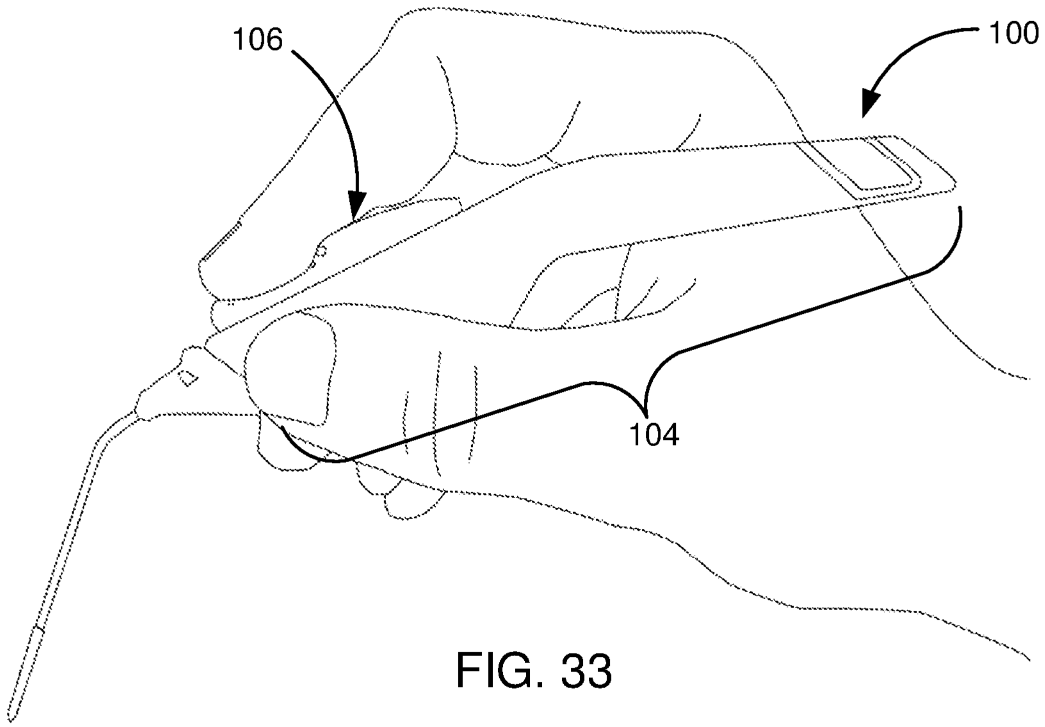
FIG. 33 illustrates a first user grip position on a handle of a tube deploying system.

FIG. 33 illustrates a first user grip position on a handle of a tube deploying system. Although FIG. 33 illustrates tube deploying system 100 shown in FIGS. 1-9, it should be realized that other tube deploying system embodiments are capable of being held with the first user grip position because each described system includes a handle 104 and pull mechanism 106. The first user grip position is a "pencil grip." As illustrated handle 104 is cradled in a user's hand like how one would cradle a pencil. The forward section of handle 104 is held between the user's thumb and middle finger, while the user's index finger engages with pull mechanism 106. The index finger will be the finger that will activate pull mechanism 106.

Figure 34:
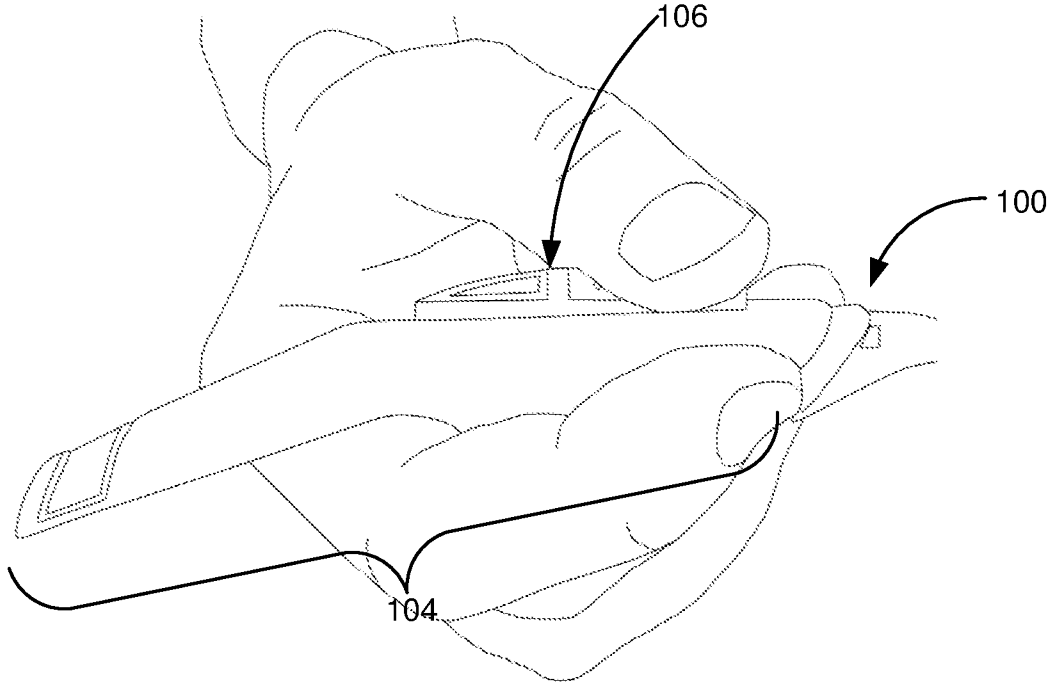
FIG. 34 illustrates a second user grip position on a handle of a tube deploying system.

FIG. 34 illustrates a second user grip position on a handle of a tube deploying system. Although FIG. 34 illustrates tube deploying system 100 shown in FIGS. 1-9, it should be realized that other tube deploying system embodiments are capable being held with the second user grip position because each described tube deploying system includes a handle 104 and pull mechanism 106. The second user grip position is a "backhand pencil grip" (or "chopstick grip"). As illustrated, handle 104 is cradled in a user's hand like how one would cradle a chopstick. The forward section of handle 104 rests between the user's index finger and the user's middle finger, while the user's thumb engages with pull mechanism 106. The thumb will be the finger that will activate pull mechanism 106.

Figure 35A:
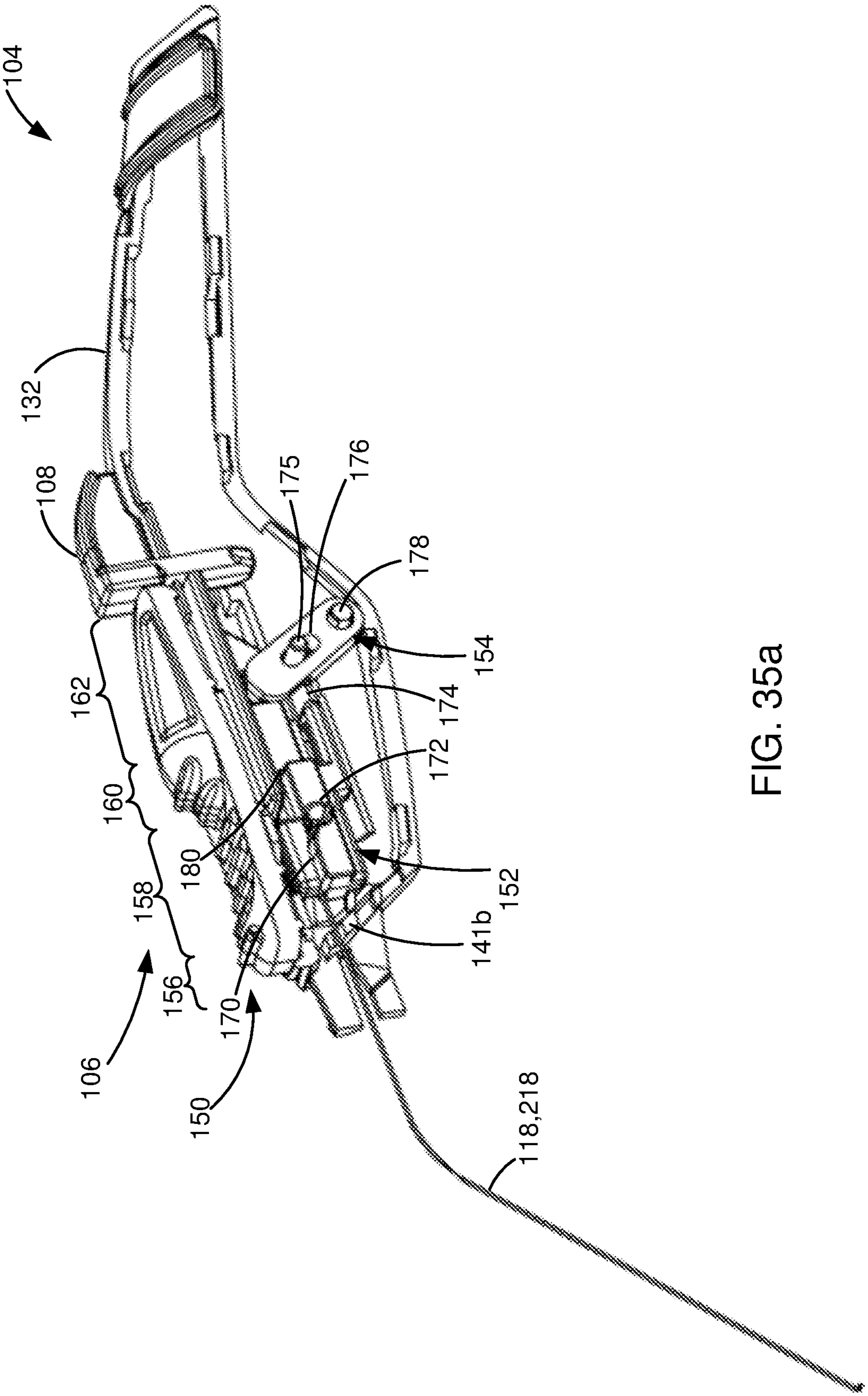
FIG. 35*a* is a perspective view of a second side housing of a handle with an embodiment of the pull mechanism in a non-pulled configuration and coupled to the actuation member.
Figure 35B:
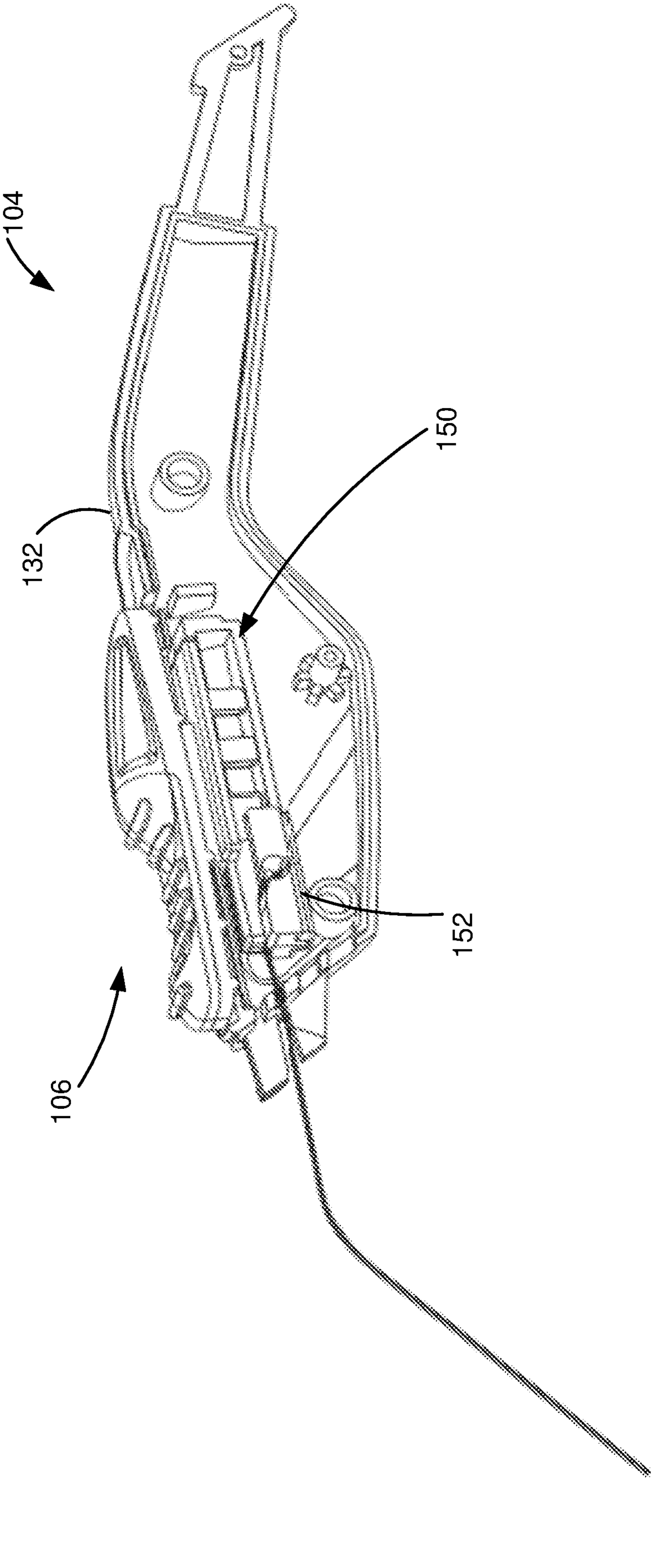
FIG. 35*b* is a perspective view of a second side housing of a handle with another embodiment of the pull mechanism in a non-pulled configuration and coupled to the actuation member.
Figure 36:
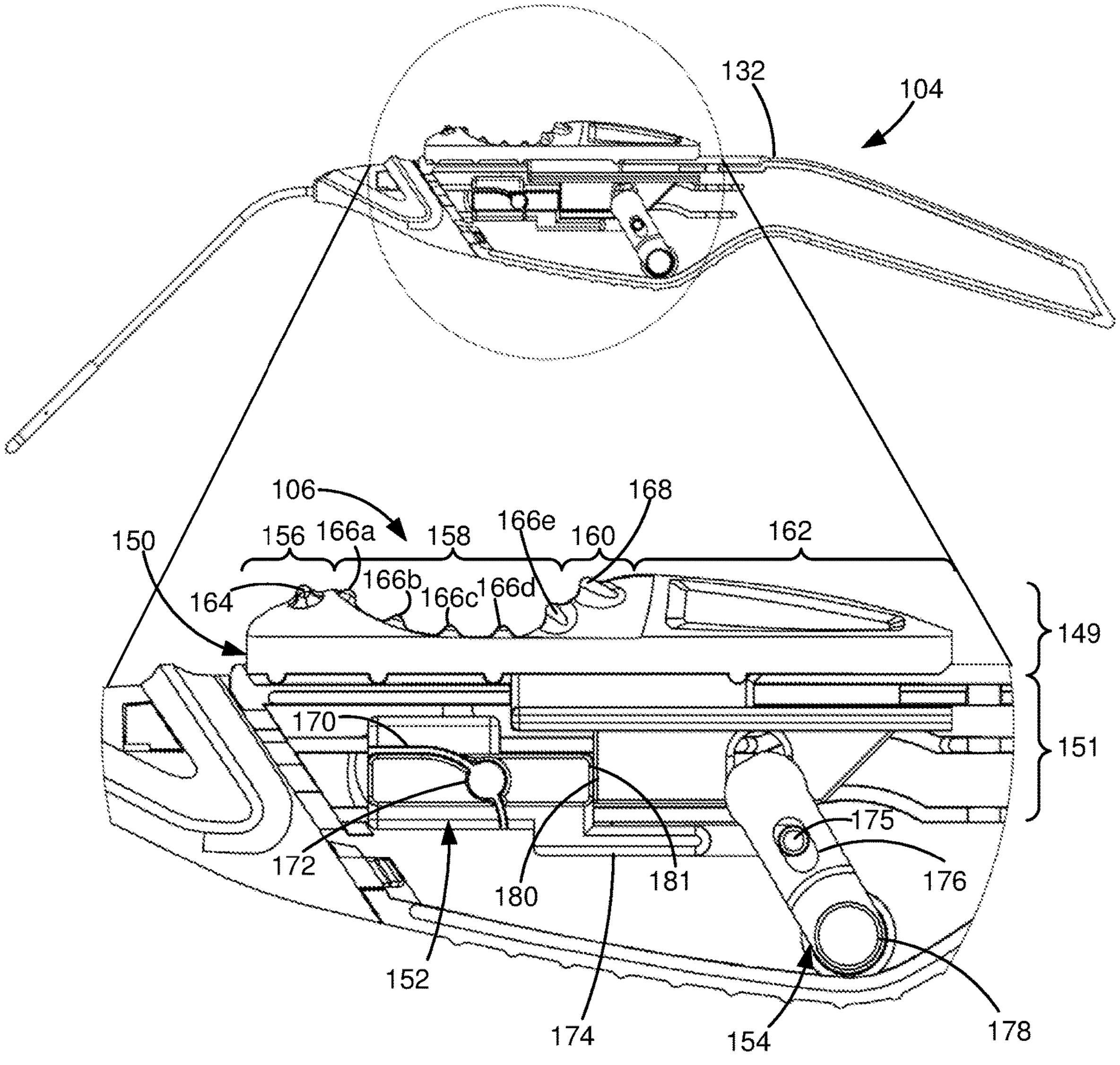
FIG. 36 is a side view of an enlarged portion of the second side housing of the handle in FIG. 35*a*.
Figure 37:
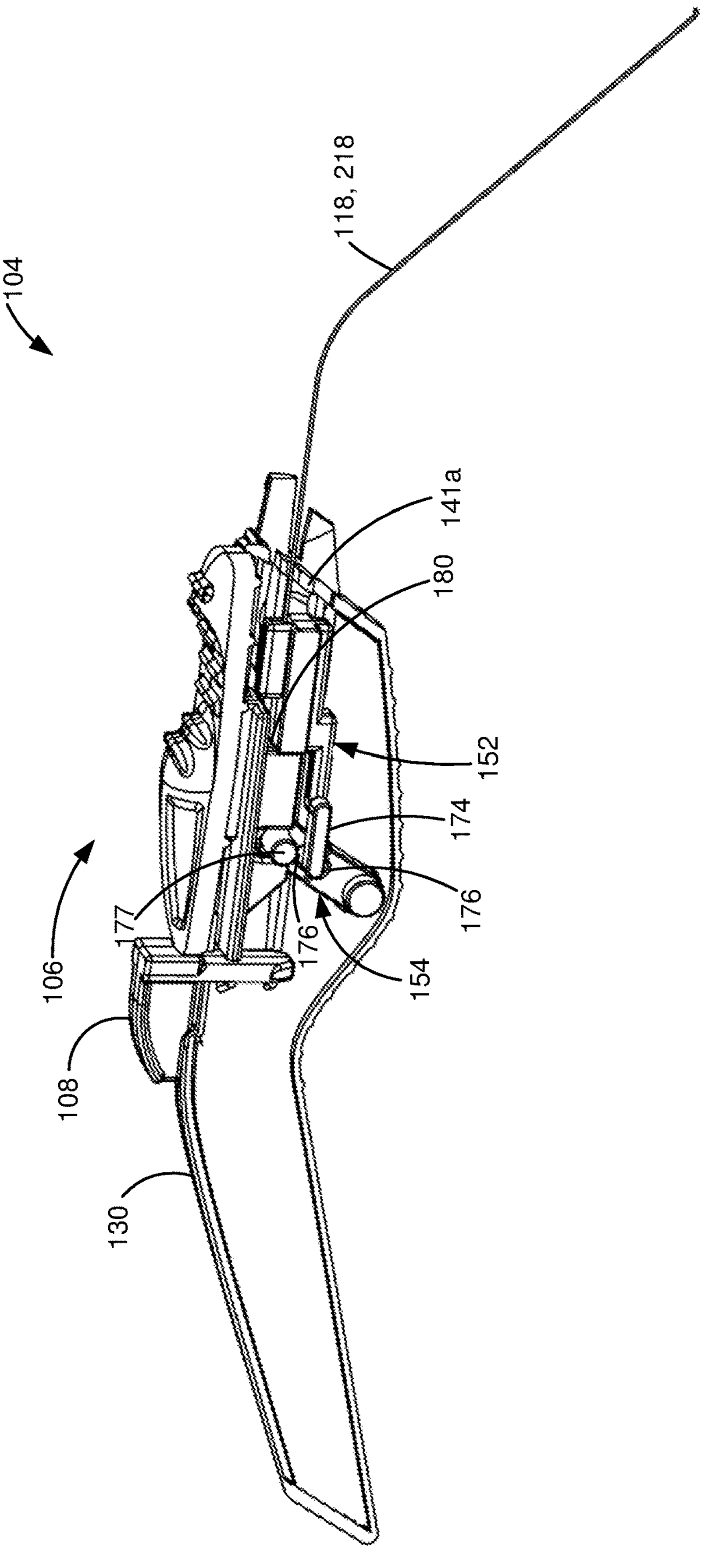
FIG. 37 is a perspective view of a first side housing of the handle with the pull mechanism in a non-pulled configuration and coupled to the actuation member.

FIG. **35*a* is a perspective view of second side housing 132 of handle 104 with pull mechanism 106 in a non-pulled configuration and coupled to actuation member 118, 218. FIG. 35*b* is an alternative embodiment of FIG. 35*a*. FIG. 36 is an enlarged view of a portion of FIG. 35*a* and FIG. 37 is a perspective view of first side housing 130 of handle 104 with pull mechanism 106 in a non-pulled configuration and coupled to actuation member 118, 218. As previously mentioned, handle 104, including pull mechanism 106, can be used with any of the embodiments of nose assemblies. Therefore, the illustrated actuation member can be of any of the described embodiments of nose assemblies. In FIGS. 35*a*, 35*b*, 36 and 37, pull mechanism 106 includes a slider 150 and a pull block 152. In FIGS. 35*a*, 36 and 37 slider 150 and pull block 152 are separate components along with a separate pivot arm 154. In FIG. 35*b*, however, slider 150 and pull block 152 are integral and therefore there is no need for pivot arm 154. Slider 150 includes an exterior or trigger portion 149 (FIG. 36) that is located outside of and protrudes from first and second side housings when coupled together. Trigger or exterior portion 149 is manually operated to move pull mechanism 106 from a non-pulled configuration to a pulled configuration. Trigger or exterior portion 149 is zoned to allow a user to tactically position their finger or thumb into locations for manual operation of pull mechanism 106. In other words, trigger 149 is zoned to receive a user's finger or thumb for manual operation. The different zones provide haptic feedback to a user on where their finger or thumb is located and also provide multiple potential finger locations per user preference. Slider 150 also includes an interior portion 151. Interior portion 151 protrudes into the interior of coupled first and second side housings 130 and 132 to provide structure for interfacing with pull block 152 and pivot arm 154 in the FIGS. 35*a*, 36 and 37 embodiment or for integrating with pull block 152 in the FIG. 35*b*** embodiment.

Exterior or trigger portion 149 of slider 150 includes a first peaked zone or region 156, a second peaked zone or region 160, a valleyed zone or region 158 between first peaked zone 156 and second peaked zone 160 and a guide zone or region 162 located behind or to the rear of second peaked zone 160. Under one embodiment, second peaked zone 160 includes a height above housings 130 and 132 that is greater than a height of first peaked zone 156. Whereas, valleyed zone 158 includes a height above housings 130 and 132 that is less than the heights of first peaked zone 156 and second peaked zone 160. First peaked zone 156, valleyed zone 158 and second peaked zone 160 include a plurality of raised features or ribs, while rear guide zone or region 162 is free of ribs and includes a smooth, backward sloping surface. The plurality of raised features provide finger or thumb locations and the smooth, backward sloping surface of rear guide zone 162 allows a user to slide their finger or thumb along the smooth, backward sloping surface to reach the plurality of raised features for finger or thumb position locations. First peaked zone 156 includes a rib 164. Valleyed zone 158 includes ribs **166*a***, *b*, *c*, *d* and *e*. Second peaked zone 160 includes rib 168. Under one user fingering positioning, a distal phalanx portion of a user's index finger rests in valleyed zone 158 with the distal tip of the index finger being located behind rib 164 as is illustrated in FIG. 33. Under another user fingering position, the distal tip of the user's index finger engages with rib 164 of first peaked zone 156. Under yet another user fingering position, a distal phalanx portion of the user's thumb rests in valleyed zone 158 with the side of the distal phalanx portion located at or behind rib 164 of first peaked zone as is illustrated in FIG. 34. The multitude and variety of ribs and zones of trigger portion 149 of slider 150 provides multiple variations of user fingering positions for manual operation of pull mechanism 106. First peaked zone 156, valleyed zone 158, or second peaked zone 160 may all serve as contact areas for an actuating thumb or finger, which maximizes the target size for locating trigger portion 149 and accounting for differences in hand size and grip styles.

Pull block 152 includes an actuation member pathway 170 and an anchoring well 172. As illustrated in FIGS. **35*a-b* and 37, actuation member 118, 218 transitions from nose assembly 102, 202 into housing 104 by exiting channel 144, 244 at back of nose 122, 222. Handle 104 includes interior structures to support actuation member 118, 218 between where actuation member 118, 218 exits channel 144, 244 and where actuation member 118, 218 is secured to pull block 152. Actuation member 118, 218 follows and is placed in pathway 170 and the proximal end of actuation member 118, 218 is coupled to or secured to pull block 152 in anchoring well 172 with, for example, an adhesive. In other embodiments, anchoring well may be a shaped well for retaining a pin to pinch the actuation member 118, 218 between the retaining pin and pull block 152 and bind actuation member 118, 218 and pull block 152 together. In other embodiments, anchoring well 172 may hold actuation member 118, 218 in a retention configuration. The interior of first side housing 130 and the interior of second side housing 132, for example, each include a wire guide 141***a* and 141*b*, respectively, that when fitted together prevents actuation member 118, 218 from buckling between channel 144, 244 and pull block 152 when compressive force is applied to actuation member 118, 218, for example, when cutting sheath 116, 216 is used to pierce the membrane.

In FIGS. 35*a*, 36 and 37, pull block 152 also includes a pull arm 174 that protrudes backwardly and has a pin 175 at the end of the pull arm 174. Pivot arm 154 includes a slot 176 that mates with pin 175 of pull arm 174 and an end pin 177 that engages with the interior portion 151 of slider 150. Pivot arm 154 is rotatably coupled to a fixed swivel or pivot point 178. The structure that provides swivel or pivot point 178 may be formed as part of either first or second side housings 130 or 132 of handle 104 or if a pin on pivot arm 154 and a deboss in the housing is used, it could be formed from both first and second side housings 130 and 132 and a pivot arm pin. In FIGS. 35*a*, 36 and 37, interior portion 151 of slider 150 includes a contact surface 180 that rigidly holds pull block 152 in place when in a full forward position or as illustrated in FIGS. 35*a*, 36 and 37, in a non-pulled configuration. In the non-pulled configuration, contact surface 180 is in direct contact with a backlash surface 181 of pull block 152. This full forward position or non-pulled configuration is further enforced by removable locking pin 108 being in place behind trigger portion 149 of slider 150. Removable locking pin 108 prevents pre-deployment of slider 150 during shipping or by a user. Overall, the full forward, non-pulled configuration where contact surface 180 of slider 150 rigidly holds pull block 152 in place and removes backlash during incision of the membrane. During incision, slider 150 is to be in a non-pulled configuration.

Figure 38:
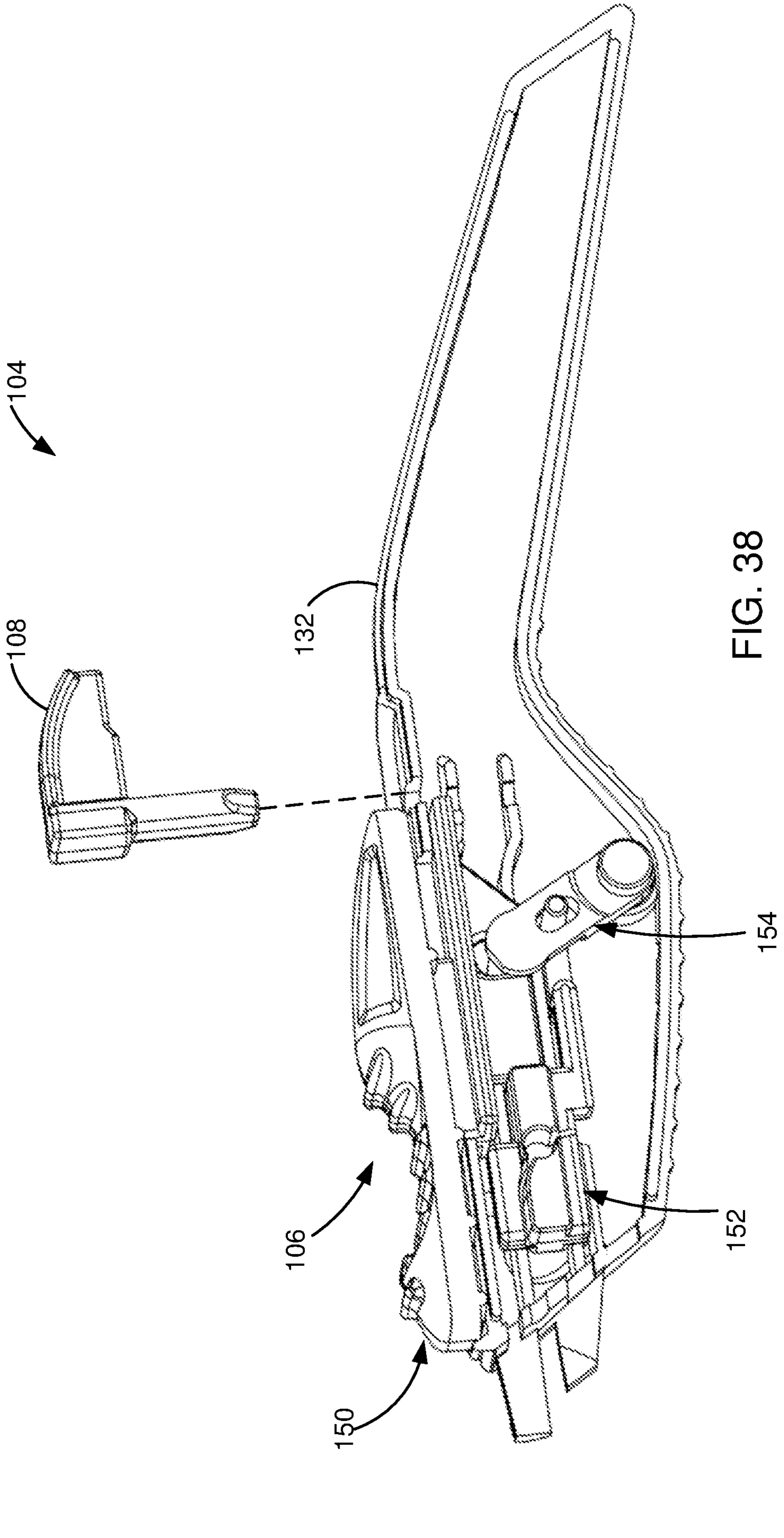
FIG. 38 is a perspective view of FIG. 35*a* without the actuation member and with the locking pin removed.

To operate the tube deploying system discussed above, tube deploying system 100, 200 is carefully removed from its packaging. Removable locking pin 108 prevents accidental movement of slider 150 so that tube deploying system 100, 200 may be inspected to make sure tube deploying system 100, 200 is not damaged. In addition, it is verified that tube 114, 214 is properly loaded within cutting sheath 116, 216 and that the portion of tube 114, 214 that protrudes through slot 115, 215 in cutting sheath 116, 216 is visible. When ready to use, removable locking pin 108 is removed as illustrated in FIG. 38.

The clinician or user grips handle 104 with one hand by tactile positioning of their fingers and/or thumb on slider 150 without moving slider 150 so as to be ready for deployment of tube 114, 214 from TTS 100, 200. As described above, the clinician may hold tube deploying system 100, 200 with the "pencil grip" as illustrated in FIG. 33, the "chopstick grip" as illustrated in FIG. 34 or other variations of these grips where the clinician is able to stabilize the operating hand holding tube deploying system 100, 200 to an ear speculum or to the patient. The clinician or user may use other parts of tube deploying system 100, 200 to grip or to stabilize. For example, nose 122, 222 includes a wing feature 123 (FIGS. 10-13), 223 (FIGS. 23-27). Wing feature 123, 223 is a rib that is formed continuously around the sides and top of nose 122 and allows the clinician or user to push forward with their fingers on nose assembly 102, 202 without slipping down nose 122, 222.

Under visualization, for example through an operating microscope or endoscope, the clinician or user manually advances or inserts nose assembly 102, 202 down the ear canal such that distal cutting edge 119, 219 of cutting sheath 116, 216 pierces and incises the membrane. The clinician or user advances nose assembly 102, 202 until medial flange of tube 114, 214 is through the membrane and the portion of tube 114, 214 that protrudes through slot 115, 215 in cutting sheath 116, 216 is visible lateral to the membrane or marker band 117, 217 on cutting sheath 116, 216 is located proximal to the membrane. In one embodiment, marker band 117, 217 is a laser mark. A laser marker adds no width to cutting sheath 116, 216 and therefore functions only as a visual aid. In another embodiment, marker band 117, 217 is a printed mark. A printed marker may be made colored and therefore functions to enhance visualization. In yet another embodiment, marker band 117, 217 may be an adhesive element or added metal element. Such an additive adds width to cutting sheath 116, 216 and therefore functions as both a visual aid, a mechanical feature to provide haptic feedback, or a mechanical stop. The length of marker band 117 along cutting sheath 116, 216 may vary depending on the tube to be deployed.

Figure 39:
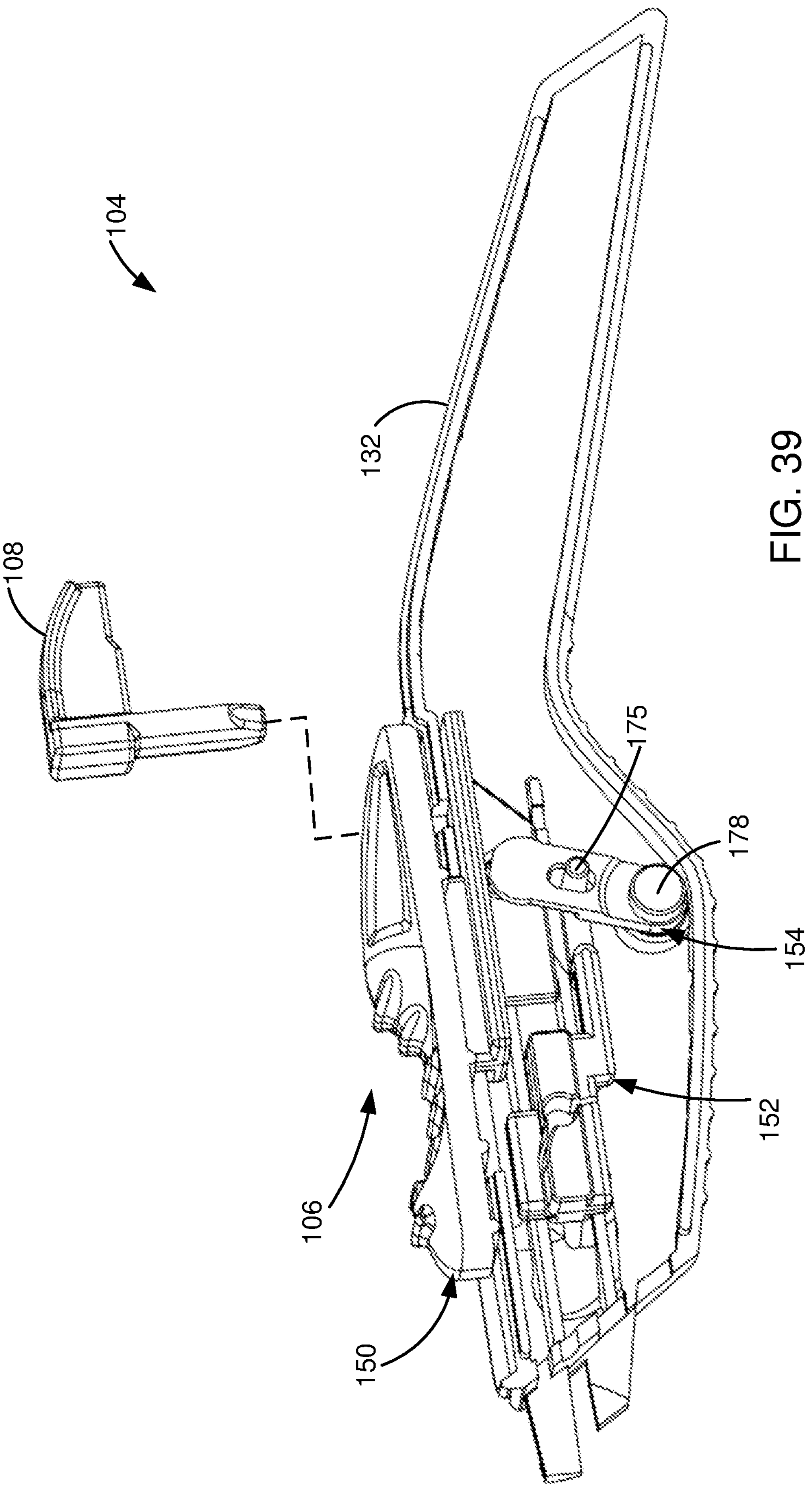
FIG. 39 is a perspective view of the second side housing of the handle of FIG. 35*a* with the locking pin removed and the pull mechanism in a pulled configuration.

The clinician or user then moves slider 150 located on handle 104 backwards away from the cutting edge 119, 219 of cutting sheath 116, 216 to retract cutting sheath 116, 216 and leave tube 114, 214 positioned across the membrane. Slider 150 is continued to be moved through its full range of motion to fully retract cutting sheath 116, 216 and until pull mechanism 106 is located in a pulled configuration as illustrated in FIG. 39. In the embodiments illustrated in FIGS. 14-32, a fully retracted cutting sheath 216 will butt up against stop 242, 342, 442.

FIG. 39 is a perspective view of the FIGS. 35*a*, 36 and 37 embodiment with first side housing 130 of handle 104 including locking pin 108 exploded and pull mechanism 106 in a pulled configuration. In particular, slider 150 is moved fully backwards from the non-pulled configuration to the pulled configuration, which causes end pin 177 (not illustrated in FIG. 39, but as previously discussed and illustrated, is directly coupled to interior portion 151 of slider 150) of pivot arm 154 to rotate pivot arm 154 about swivel or pivot point 178. This rotation of pivot arm 154 causes pull arm 152 at pin 175 to pull backwards and therefore pull actuation member 118, 218 along with pull block 152 to retract distal cutting edge 119, 219 and deploy tube 114, 214. Actuation member 118, 218 is coupled to cutting sheath 116, 216 and retracts cutting sheath 116, 216. It should be realized that there may be variations in pivot arm 154 in terms of length and location of where pin 177 interfaces with slider 150. For example, in the illustrated embodiment, trigger 149 of slider 150 travels approximately 1.5 times further than distal cutting edge 119, 219. However, other ratios are possible including a 1:1 ratio between slider 150 and distal cutting edge 119, 219.

Figure 40:
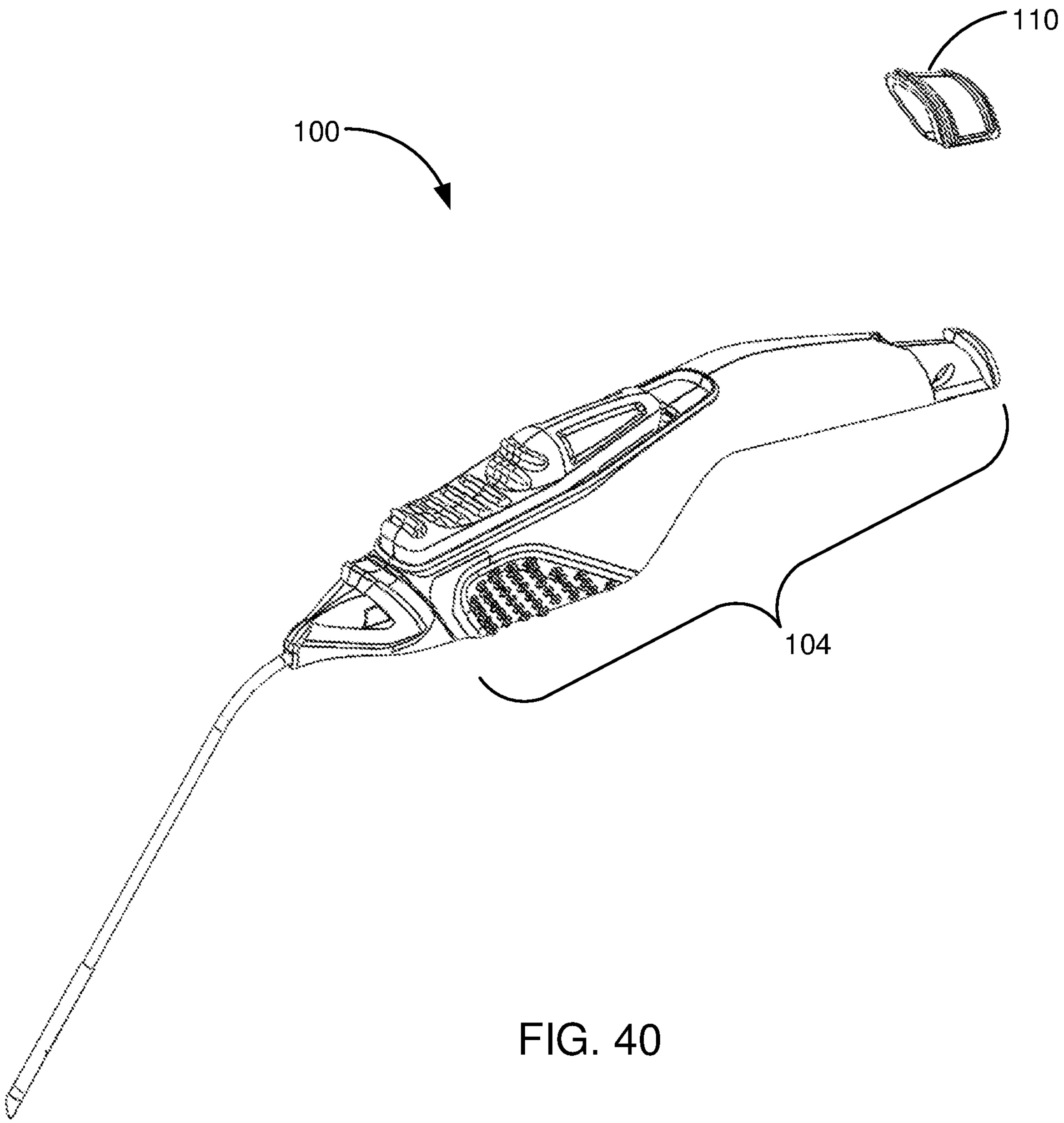
FIGS. 40-42 illustrate a process of disassembling the handle and disassembling the nose assembly from the handle so as to reduce the amount of sharps waste and/or allow easier disposal and recycling.
Figure 41:
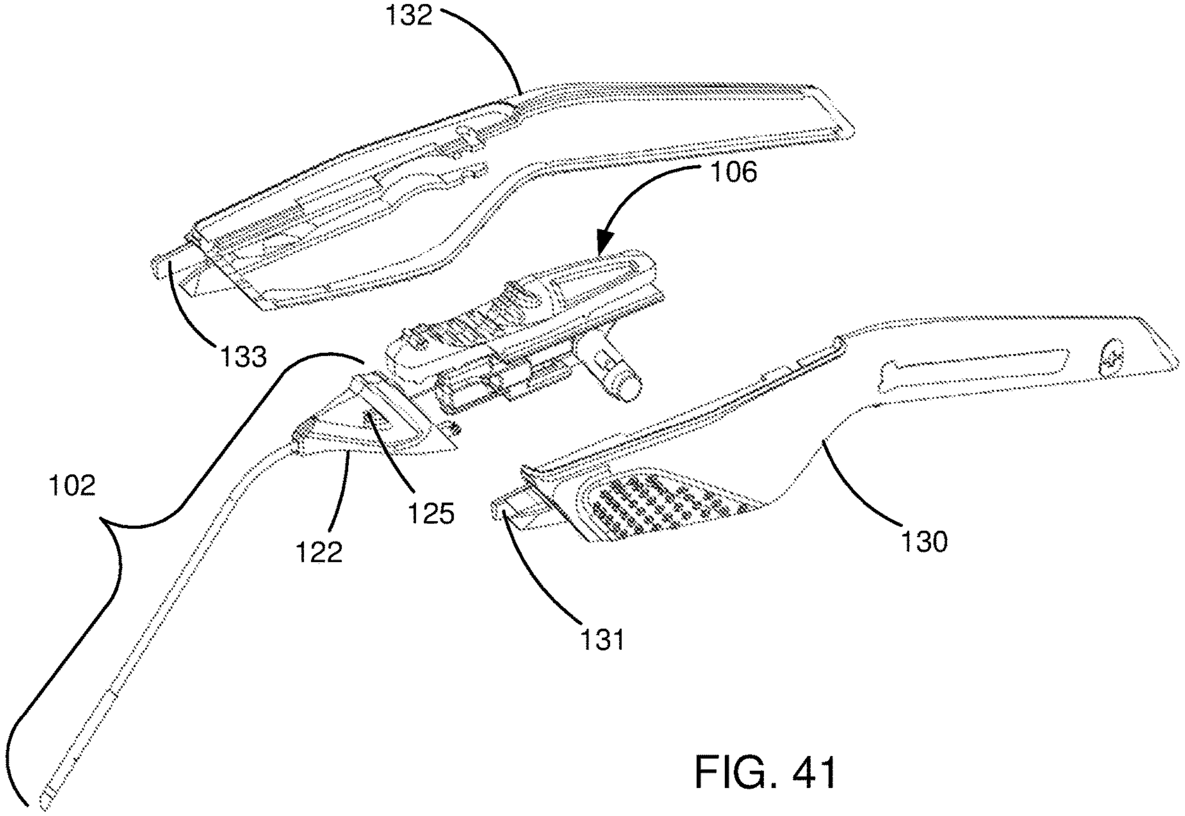
Figure 42:
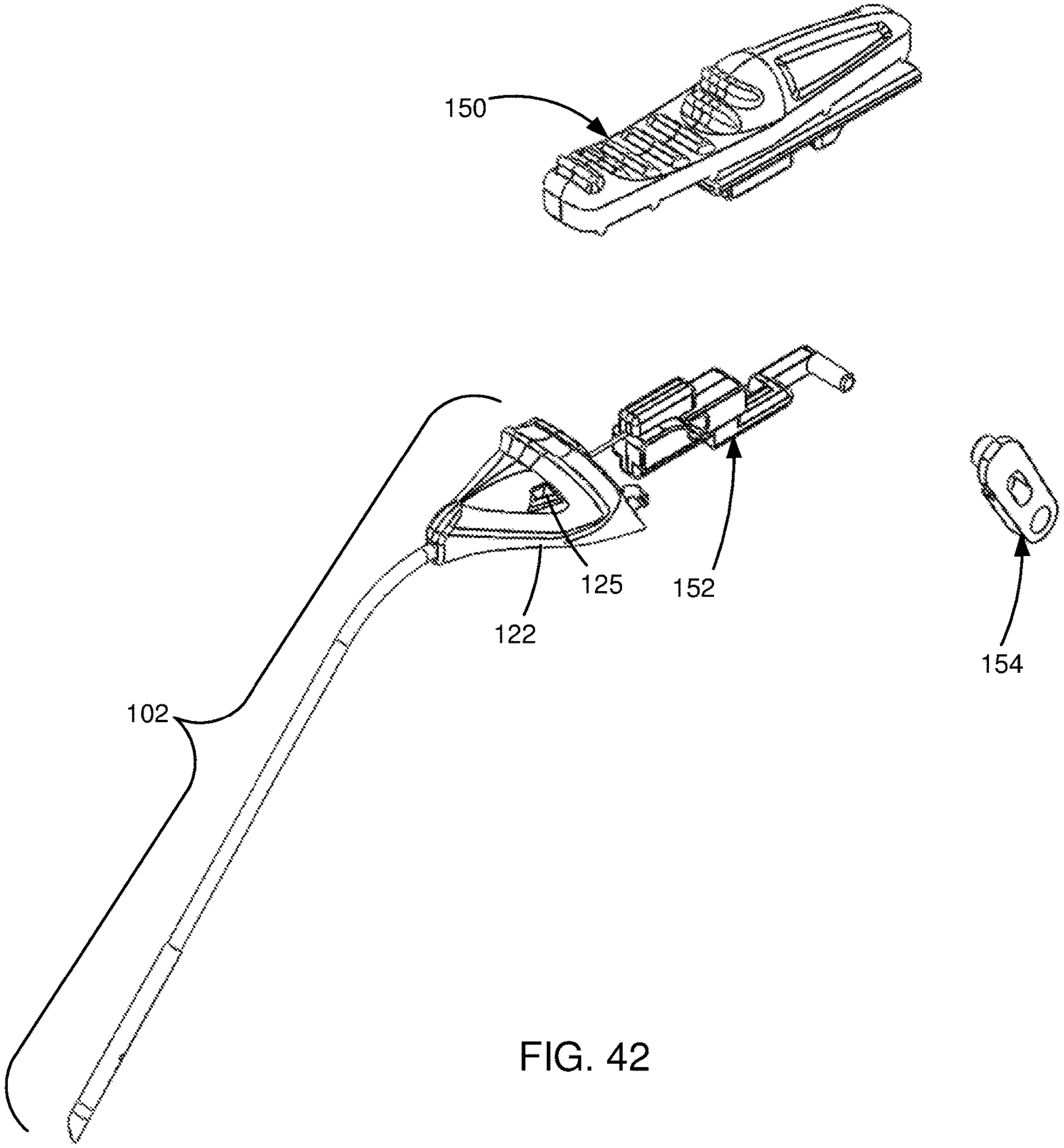

Once tube 114, 214 is deployed in the membrane and free of cutting sheath 116, 216, TTS 100, 200 is removed from the ear canal and disposed of appropriately. To facilitate proper waste disposal, the entirety of tube deploying system 100, 200 would be considered to be sharps waste if all kept together. Sharps waste is a form of biomedical waste that is composed of "sharps," which includes any device or object used to puncture or lacerate a membrane. Sharps waste is classified as biohazardous waste and must be carefully handled. By breaking tube deploying system 100, 200 down into sharps waste and normal waste, the quantity of sharps waste can be reduced. FIGS. 40-42 illustrate a process of disassembling embodiments of a handle and specifically exemplifying the disassembly of a nose of a nose assembly from the handle so as to reduce the amount of sharps waste.

In FIG. 40, removable assembly clip 110 is removed from handle 104 and is no longer considered to be sharps waste. In FIG. 41, the embodiment of handle 104 does not include removable assembly clip 110, but does include first side housing 130 and second side housing 132, which are separated from pull mechanism 106 and nose assembly 102. In particular, snap-on feature 131 on first side housing 130 is freed from through hole 125 on nose 122 and snap-on feature 133 on second side housing 132 is freed from through hole 127 on nose 122. In addition, swivel point 178 on second side housing 132 is freed from pivot arm 154 of pull mechanism 106. Because first side housing 130 and second side housing 132 are separated from pull mechanism 106 and nose assembly 102, first side housing 130 and second side housing 132 are no longer considered to be sharps waste. In FIG. 42, pivot arm 154 is separated from pull block 152 and slider 150. With this action, pivot arm 154 and slider 150 are free from pull block 152 and nose assembly 102 and no longer considered to be sharps waste. The remaining nose assembly 102 and pull block 152 are now disposed of in sharps waste, which is a reduction in sharps waste compared to when tube deploying system 100 was entirely assembled.

Although elements have been shown or described as separate embodiments above, portions of each embodiment may be combined with all or part of other embodiments described above. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A tube deploying system comprising:

a nose assembly including a distal cutting edge and a tube, wherein the distal cutting edge is configured to be manually advanced to pierce a membrane of a patient;

a handle including a distal end coupled to the nose assembly, a proximal end and a pull mechanism having a slider comprising a single, continuous body and a pull block comprising a single, continuous body separate from the single, continuous body of the slider, wherein the slider has a first portion that protrudes from an outer surface of the handle and a second portion located inside the handle and having a contact surface, and wherein the pull block is located inside the handle and includes a backlash surface; and an actuation member having a distal end that couples to the distal cutting edge and a proximal end that directly couples to the pull block;

wherein when the pull mechanism is in a non-pulled configuration the slider is in a full forward position such that the contact surface of the second portion of the slider directly contacts the backlash surface of the pull block and is configured to rigidly hold the pull block in the full forward position; and wherein when the pull mechanism is in a pulled configuration the slider is manually operated to be slidable relative to the handle in a direction from the distal end of the handle to the proximal end of the handle and the slider is configured to pull the pull block and the actuation member so that the distal cutting edge retracts to deploy the tube, wherein in the pulled configuration the contact surface of the second portion of the slider decouples from the backlash surface of the pull block.

2. The tube deploying system of claim 1, wherein the pull mechanism further comprises a pivot arm that comprises a single, continuous body separate from the single continuous body of the slider and the single, continuous body of the pull block and is rotatable about a fixed pivot point and is directly coupled to the pull block and directly coupled to the second portion of the slider, wherein in the pulled configuration the slider rotates the pivot arm about the fixed pivot point to pull the pull block and the actuation member such that the distal cutting edge is retracted to deploy the tube.

3. The tube deploying system of claim 1, wherein a range of mechanical advantage between the manually operated slider and the retraction of the distal cutting edge comprises 1:1 to 1.5:1.

4. The tube deploying system of claim 1, wherein the first portion of the slider comprises a trigger portion and is configured to receive a finger or thumb of a user, the trigger portion including a first peaked zone, a second peaked zone located between the proximal end of the handle and the first peaked zone, a valleyed zone located between the first peaked zone and the second peaked zone and a rear guide zone located between the second peaked zone and the proximal end of the handle.

5. The tube deploying system of claim 4, wherein the first peaked zone, the second peaked zone and the valleyed zone include a plurality of raised features and the rear guide zone is free of the plurality of raised features.

6. The tube deploying system of claim 4, wherein the second peaked zone comprises a height that is greater than a height of the first peaked zone.

7. The tube deploying system of claim 6, wherein the valleyed zone comprises a height that is less than the heights of the first peaked zone and the second peaked zone.

8. A tube deploying system comprising:

a nose assembly including a distal cutting edge and a tube, wherein the distal cutting edge is configured to be manually advanced to pierce a membrane of a patient;

a handle having a housing that includes a distal end coupled to the nose assembly and a proximal end, wherein the handle comprises a pull mechanism that includes a pull block comprising a single, continuous body located inside of the housing and a slider comprising a single, continuous body separate from the single, continuous body of the pull block, the slider having an exterior portion located on an exterior of the housing and an interior portion located inside the housing; and an actuation member having a distal end that couples to the distal cutting edge and a proximal end that directly couples to the pull block;

wherein the exterior portion of the slider includes a trigger that is configured to be manually operated to slide the interior and exterior portions of the slider from a non-pulled configuration that is in a distal position to a pulled configuration that is in a proximal position;

wherein in the non-pulled configuration the interior portion of the slider is coupled to the pull block at a first direct coupling and a different second coupling;

wherein in the pulled configuration the interior portion of the slider is decoupled at the first direct coupling and spaced apart from the pull block and the interior portion of the slider remains coupled to the pull block at the second coupling to pull the pull block and therefore the actuation member using the second coupling such that the distal cutting edge is retracted to deploy the tube.

9. The tube deploying system of claim 8, wherein the trigger of the slider comprises:

a first peaked zone;

a second peaked zone located between the proximal end of the housing and the first peaked zone;

a valleyed zone located between the first peaked zone and the second peaked zone;

a rear guide zone located between the second peaked zone and the proximal end of the housing;

wherein the first peaked zone, the second peaked zone and the valleyed zone include a plurality of raised features and the rear guide zone is free of the plurality of raised features.

10. The tube deploying system of claim 9, wherein the second peaked zone comprises a height that is greater than a height of the first peaked zone.

11. The tube deploying system of claim 9, wherein the valleyed zone comprises a height that is less than heights of the first peaked zone and the second peaked zone.

12. The tube deploying system of claim 8, further comprising a pivot arm that is rotatable about a fixed pivot point and provides the second coupling to couple the pull block to the interior portion of the slider.

13. The tube deploying system of claim 12, wherein when the slider operates to pull the pull block from the non-pulled configuration to the pulled configuration the slider rotates the pivot arm about the fixed pivot point to pull the pull block and the actuation member at the second coupling.

14. The tube deploying system of claim 8, wherein the interior portion of the slider comprises a contact surface and the pull block comprises a backlash surface, wherein in the non-pulled configuration the first direct coupling comprises the contact surface of the interior portion of the slider being in direct contact with the backlash surface of the pull block to reduce backlash in the pull mechanism.

15. A tube deploying system comprising:

a nose assembly including a nose portion, an elongated portion, a distal cutting edge and a tube, wherein at least some of the elongated portion, the distal cutting edge and the tube are configured to be advanced into an orifice of a patient so that the distal cutting edge pierces a membrane of the patient;

a handle including a housing having a distal end and a proximal end and a pull mechanism, wherein the pull mechanism has a pull block comprising a single, continuous body that is coupled to a slider comprising a single, continuous body at a first direct coupling and a different second coupling; and an actuation member having a distal end that couples to the distal cutting edge and a proximal end that directly couples to the pull block; and wherein the slider includes a trigger portion located on an exterior of the housing and an interior portion located in an interior of the housing, wherein upon the trigger portion being manually operated the interior portion of the slider is configured to decouple at the first direct coupling and be spaced apart from the pull block and configured to rotate a pivot arm located inside the housing that couples the slider to the pull block at the second coupling, the pivot arm being configured to rotate about a fixed pivot point so as to pull the pull block at the second coupling and therefore pull the actuation member coupled to the pull block to retract the distal cutting edge and deploy the tube.

16. The tube deploying system of claim 15, wherein the trigger portion on the slider comprises tactile positioning features.

17. The tube deploying system of claim 15, further comprising a locking pin located between the trigger portion of the slider and the proximal end of the housing, wherein the locking pin is configured to prevent movement of slider before the nose assembly is advanced into the orifice of the patient.

18. The tube deploying system of claim 15, further comprising a removable clip located at the proximal end of the housing that is configured to disassemble the housing from around the pull mechanism so that the slider and the pivot arm are capable of being separated from the nose assembly and the pull block.

* * * * *